(12) United States Patent
Pfeiffer et al.

(10) Patent No.: US 7,640,978 B2
(45) Date of Patent: Jan. 5, 2010

(54) BIOGENIC FUEL GAS GENERATION IN GEOLOGIC HYDROCARBON DEPOSITS

(75) Inventors: Robert S. Pfeiffer, Parker, CO (US); Glenn Ulrich, Golden, CO (US); Gary Vanzin, Arvada, CO (US); Verlin Dannar, Sheridan, WY (US); Roland P. DeBruyn, Highlands Ranch, CO (US); James B. Dodson, Castle Rock, CO (US)

(73) Assignee: LUCA Technologies, Inc., Golden, CO (US)

(*) Notice: Subject to any disclaimer, the term of this patent is extended or adjusted under 35 U.S.C. 154(b) by 0 days.

(21) Appl. No.: 12/136,728

(22) Filed: Jun. 10, 2008

(65) Prior Publication Data

US 2008/0299635 A1 Dec. 4, 2008

Related U.S. Application Data

(63) Continuation of application No. 11/343,429, filed on Jan. 30, 2006, now Pat. No. 7,426,960, which is a continuation-in-part of application No. PCT/US2005/015259, filed on May 3, 2005.

(51) Int. Cl.
*E21B 43/22* (2006.01)
*C09K 8/58* (2006.01)

(52) U.S. Cl. .............. 166/246; 507/201; 428/243
(58) Field of Classification Search .............. None
See application file for complete search history.

(56) References Cited

U.S. PATENT DOCUMENTS

| 1,990,523 A | 2/1935 | Buswell et al. |
| 2,413,278 A | 12/1946 | Zobell |
| 2,641,566 A | 6/1953 | Zobell |
| 2,659,659 A | 11/1953 | Schmidl |
| 2,660,550 A | 11/1953 | Updegraff et al. |
| 2,807,570 A | 9/1957 | Updegraff |
| 2,907,389 A | 10/1959 | Hitzman |
| 2,975,835 A | 3/1961 | Bond |
| 3,006,755 A | 10/1961 | Adams |
| 3,185,216 A | 5/1965 | Hitzman |
| 3,332,487 A | 7/1967 | Jones |

(Continued)

FOREIGN PATENT DOCUMENTS

DE 4036787 B1 5/1992

(Continued)

OTHER PUBLICATIONS

Aitken, Carolyn M. et al "Anaerobic hydrocarbon degradation in deep subsurface oil reserves" Nature, Sep. 16, 2004, pp. 291-294.
Anderson, Robert T., and Lovley, Derek R., "Hexadecane Decay by Methanogenesis", Nature, v. 404, p. 722, Apr. 13, 2000.
Anderson, Robert T., Rooney-Varga, Juliette N., et al., "Anaerobic Benzene Oxidation in the Fe(III) Reduction Zone of Petroleum-Contaminated Aquifers", Environmental Science & Technology, v. 32, pp. 1222-1229, 1998.

(Continued)

*Primary Examiner*—Zakiya W. Bates
(74) *Attorney, Agent, or Firm*—Townsend and Townsend and Crew LLP

(57) ABSTRACT

A method for stimulating methane production from a carbonaceous material is described. The methods may include the step of contacting the material with cells of a methanogenic consortium under anaerobic conditions to form a reaction mixture. The method may also include maintaining anaerobic conditions for a time sufficient to permit methanogenesis, and collecting methane from anaerobic water or head space of the reaction mixture.

11 Claims, 11 Drawing Sheets

U.S. PATENT DOCUMENTS

| | | |
|---|---|---|
| 3,340,930 A | 9/1967 | Hitzman |
| 3,437,654 A | 4/1969 | Dix |
| 3,637,686 A | 1/1972 | Kokubo et al. |
| 3,640,846 A | 2/1972 | Johnson |
| 3,724,542 A | 4/1973 | Hamilton |
| 3,800,872 A | 4/1974 | Friedman |
| 3,826,308 A | 7/1974 | Compere-Whitney |
| 3,982,995 A | 9/1976 | Yen et al. |
| 4,184,547 A | 1/1980 | Klass et al. |
| 4,300,632 A | 11/1981 | Wilberger et al. |
| 4,316,961 A | 2/1982 | Klass et al. |
| 4,329,428 A | 5/1982 | Ghosh et al. |
| 4,349,633 A | 9/1982 | Worne et al. |
| 4,358,535 A | 11/1982 | Falkow et al. |
| 4,358,537 A | 11/1982 | Chynoweth |
| 4,386,159 A | 5/1983 | Kanai |
| RE31,347 E | 8/1983 | Reijonen et al. |
| 4,416,332 A | 11/1983 | Wiberger et al. |
| 4,424,064 A | 1/1984 | Klass et al. |
| 4,446,919 A | 5/1984 | Hitzman |
| 4,450,908 A | 5/1984 | Hitzman |
| 4,475,590 A | 10/1984 | Brown |
| 4,481,293 A | 11/1984 | Thomsen et al. |
| 4,522,261 A | 6/1985 | McInerney et al. |
| 4,562,156 A | 12/1985 | Isbister et al. |
| 4,579,562 A | 4/1986 | Tarman et al. |
| 4,610,302 A | 9/1986 | Clark |
| 4,640,767 A | 2/1987 | Zajic et al. |
| 4,666,605 A | 5/1987 | Minami et al. |
| 4,678,033 A | 7/1987 | Killough |
| 4,799,545 A | 1/1989 | Silver et al. |
| 4,826,769 A | 5/1989 | Menger |
| 4,845,034 A | 7/1989 | Menger et al. |
| 4,883,753 A | 11/1989 | Belaich et al. |
| 4,905,761 A | 3/1990 | Bryant |
| 4,906,575 A | 3/1990 | Silver et al. |
| 4,914,024 A | 4/1990 | Strandberg et al. |
| 4,947,932 A | 8/1990 | Silver et al. |
| 4,971,151 A | 11/1990 | Sheehy |
| 5,044,435 A | 9/1991 | Sperl et al. |
| 5,076,927 A | 12/1991 | Hunter |
| 5,083,610 A | 1/1992 | Sheehy |
| 5,083,611 A | 1/1992 | Clark et al. |
| 5,087,558 A | 2/1992 | Webster, Jr. |
| 5,100,553 A | 3/1992 | Nomura et al. |
| 5,163,510 A | 11/1992 | Sunde |
| 5,297,625 A | 3/1994 | Premuzic et al. |
| 5,327,967 A | 7/1994 | Jenneman et al. |
| 5,340,376 A | 8/1994 | Cunningham |
| 5,341,875 A | 8/1994 | Jenneman et al. |
| 5,350,684 A | 9/1994 | Nakatsugawa et al. |
| 5,360,064 A | 11/1994 | Jenneman et al. |
| 5,363,913 A | 11/1994 | Jenneman et al. |
| 5,368,099 A | 11/1994 | Davey et al. |
| 5,424,195 A | 6/1995 | Volkwein |
| 5,492,828 A | 2/1996 | Premuzic et al. |
| 5,500,123 A | 3/1996 | Srivastava |
| 5,510,033 A | 4/1996 | Ensley et al. |
| 5,516,971 A | 5/1996 | Hurley |
| 5,538,530 A | 7/1996 | Heaton et al. |
| 5,551,515 A | 9/1996 | Fodge et al. |
| 5,560,737 A | 10/1996 | Schuring et al. |
| 5,593,886 A | 1/1997 | Gaddy |
| 5,597,730 A | 1/1997 | Aust et al. |
| 5,630,942 A | 5/1997 | Steiner |
| 5,670,345 A | 9/1997 | Srivastava et al. |
| 5,695,641 A | 12/1997 | Cosulich et al. |
| 5,723,597 A | 3/1998 | Kohne |
| 5,763,736 A | 6/1998 | Daume |
| 5,854,032 A | 12/1998 | Srivastava et al. |
| 5,858,766 A | 1/1999 | Premuzic et al. |
| 5,885,825 A | 3/1999 | Lin et al. |
| 5,919,696 A | 7/1999 | Ikeda et al. |
| 5,928,864 A | 7/1999 | Kohne |
| 5,955,261 A | 9/1999 | Kohne |
| 5,955,262 A | 9/1999 | Kourilsky et al. |
| 6,090,593 A | 7/2000 | Fleming et al. |
| 6,143,534 A | 11/2000 | Menger et al. |
| 6,202,051 B1 | 3/2001 | Woolston |
| 6,210,955 B1 | 4/2001 | Hayes |
| 6,265,205 B1 | 7/2001 | Hitchens et al. |
| 6,543,535 B2 | 4/2003 | Converse et al. |
| 6,758,270 B1 | 7/2004 | Sunde et al. |
| 6,795,922 B2 | 9/2004 | Johnson et al. |
| 6,859,880 B2 | 2/2005 | Johnson et al. |
| 2001/0045279 A1 | 11/2001 | Converse et al. |
| 2002/0102673 A1 | 8/2002 | Zhang et al. |
| 2003/0062270 A1 | 4/2003 | McAlister |
| 2003/0205458 A1 | 11/2003 | Roychowdhury |
| 2004/0033557 A1 | 2/2004 | Scott et al. |
| 2004/0035785 A1 | 2/2004 | Rebholz |
| 2005/0053955 A1 | 3/2005 | Sowlay et al. |
| 2006/0223153 A1* | 10/2006 | Pfeiffer et al. ............... 435/166 |
| 2007/0092930 A1 | 4/2007 | Lal et al. |

FOREIGN PATENT DOCUMENTS

| | | |
|---|---|---|
| DE | 4115435 B2 | 8/1992 |
| DE | 19520548 B3 | 12/1996 |
| JP | 09 121868 B4 | 5/1997 |
| WO | WO 79/00201 B5 | 4/1979 |
| WO | WO 89/10463 A1 | 11/1989 |
| WO | WO 92/13172 A1 | 8/1992 |
| WO | WO 01/68904 B6 | 9/2001 |
| WO | WO 02/34931 A2 | 5/2002 |

OTHER PUBLICATIONS

Artech Inc., Biological Gasification of Coals. Final Report, U.S. Department of Energy, Contract DE-AC21-87MC23285, pp. 40-63, 1990.

Basiliko, Nathan et al. "Influence of Ni, Co, Fe, and Na additions on methane production in Sphagnum dominated Northern American peatlands" Biogeochemistry, 2001, 52: 133-153.

Belyaev, S. S., et al. "Methanogenic Bacteria from the Bondyuzhskoe Oil Field: General Characterization and Analysis of Stable-Carbon Isotopic Fractionation" Applied and Environmental Microbiology, 1983, v. 45, No. 2, pp. 691-697.

Bernard, F. P., et al. "Indigenous Microorganisms in Connate Water of Many Oil Fields: A New Tool in Exploration and Production Techniques" SPE 24811, 1992, pp. 467-476.

Boone, David R. et al.-Bergey's Manual of Systematic Bacteriology-Second Edition- vol. One "The Archaea and the Deeply Branching and Phototrophic Bacteria", Springer, 4 pages.

Brockman, Fred "Regulation of Microbial Communities" at http://www.sysbio.org/sysbio/microbial/index.stm, 2005, 2 pages.

Brown, L.R., and Vadie, A.A., "Slowing Production Decline and Extending the Economic Life of an Oil Field: New MEOR Technology", SPE 59306; SPE/DOE Improved Oil Recovery Symposium, Tulsa, Oklahoma, Apr. 3-5, 2000.

Budwill, Karen "Microbial Methanogenesis and its Role in Enhancing Coalbed Methane Recovery" (Canadian Coals) CSEG Recorder (Nov. 2003) pp. 41-43.

Cervantes, Francisco J. et al, "Competition between methanogenesis and quinone respiration for ecologically important substrates in anaerobic consortia" FEMS Microbiology Ecology 34, 2000, pp. 161-171.

Claypool, George E. et al. "The Origin and Distribution of Methane in Marine Sediments" *Natural Gases in Marine Sediments*, Ed. Isaac R. Kaplan, 1974, pp. 99-139.

Claypool, George E. "Geochemical Characterization of Biogenic Gas and Coalbed Methane in Shallow Gas Fields: Eastern Denver Basin, Powder River Basin and Williston Basin" Luca Technologies, Inc. Internal Report, Jul. 8, 2001, 29 pages.

Clayton et al. "Oil-Generating Coals of the San Juan Basin, New Mexico and Colorado, U.S." Org. Geochem. 1991, pp. 735-742, vol. 17, No. 6.

Clayton, C. et al. "Source Volumetrics of Biogenic Gas Generation" Bacterial Gas, Ed. R. Vially, 1992, pp. 191-204, Paris.

Coates, John D., Anderson, Robert T., et al., "Anaerobic Hydrocarbon Degradation in Petroleum-Contaminated Harbor Sediments under Sulfate-Reducing and Artificially Imposed Conditions", Environ. Sci. Technol., vol. 30, No. 9, pp. 2784-2789, 1996.

Connan, J. et al. Anaerobic biodegradation of petroleum in reservoirs: a widespread phenomenon in nature: 18th International Meeting on Organic Geochemistry Sep. 22-26, 1997 Maastricht, The Netherlands (Abstr.), p. O2: 5-6.

Connan, J. et al. "Origin of Gases in Reservoirs" 1995 International Gas Research Conference, 1996, pp. 21-41.

Conrad, R. "Contribution of hydrogen to methane production and control of hydrogen concentrations in methanogenic soils and sediments" FEMS Microbiology Ecology, 28 (1999) pp. 193-202.

DeBruin, R.H. et al. "Coalbed Methane In Wyoming" Wyoming State Geological Survey (Laramie, WY), Information Pamphlet 7 (second revision), 2004, 24 pages.

Donaldson et al., "Conference Focuses on Microbial Enhancement of Oil Recovery," The Oil and Gas Journal, pp. 47-52, Dec. 20, 1982.

Donaldson, Eric C. et al. Microbial Enhanced Oil Recovery, Developments in Petroleum Science, 1989, v. 22, pp. 1-14, 121, 123, 149, Elsevier.

Faber, E. et al. "Distinction of Bacterial and Thermogenic Hydrocarbon Gases" Bacterial Gas, Ed. R. Vially, 1992, pp. 63-74, Paris.

Flesner, R. et al. "Pilot-scale base hydrolysis processing of HMX-based plastic-bonded explosives", 4th International Symposium on Special Topics in Chemical Propulsion: Challenges In Propellants and 100 Years After Nobel, May 27-31, 1996, pp. 213-220.

Flesner, R. et al. "Pilot-scale base hydrolysis processing of HMX-based plastic-bonded explosives", Chemical Abstracts, vol. 130, No. 5, Feb. 1, 1998, Columbus, Ohio, U.S.; Abstract No. 54464a, pp. 835.

Gaasterland, Terry "Archaeal Genomics" Current Opinions in Microbiology (1999) 2:542-547.

Galagan, James, E. et al. "The Genome of *M. acetivorans* Reveals Extensive Metabolic and Physiological Diversity" Genome Research 12: 532-542 (2002).

Grbic-Galic, D., and Vogel, T. "Transformation of Toluene and Benzene by mixed methanogenic cultures" Applied and Environmental Microbiology, 1987, v. 53, pp. 254-260.

Groudeva, V. I. et al. "Enhanced Oil Recovery by Stimulating the Activity of the Indigenous Microflora of Oil Reservoirs": Biohydrometallurgical Technologies (Eds. Torma, A. E., Apel, M.L.; and Brierlay, C.L.): Minerals, Metals, & Mater. Soc. Biohydromet. Technol. Int. Symp, 1993 (Jackson Hole, Wy. 93.8.22-25) Proc., v. 2, pp. 349-356.

Gullapalli, Irene L. et al., "Laboratory Design and Field Implementation of Microbial Profile Modification Process", SPE Reservoir Evaluation & Engineering, v. 3, No. 1, pp. 42-49, Feb. 2000.

Halbouty, M.T. "East Texas Field—USA, East Texas Basin, Texas; in Stratigraphic Traps II" (compiled by N.H. Foster, and E.A. Beaumont) AAPG Treatise of Petroleum Geology, Atlas of Oil and Gas Fields, 1991, pp. 189-206.

Hales, B.A. et al. "Isolation and Identification of Methanogen-specific DNA from Blanket Bog Peat by PCR Amplification and Sequence Analysis", Applied and Environmental Microbiology, 1996, pp. 668-675.

Hattori, Satoshi et al.; "*Thermacetogenium phaeum* gen.nov.,sp.nov., a strictly anaerobic, thermophilic, syntrophic acetate-oxidizing bacterium", Internation. Journal of Systematic and Evolutionary Microbiology (2000), 50, 1601-1609, 9 pages, 2000.

Hermann, M. et al. "Anaerobic Microflora of Oil Reservoirs: Microbiological Characterization of Samples from Some Production Wells" Bacterial Gas (R. Vially Ed.) Editions Technip. Paris, 1992, pp. 223-233.

Hunkeler et al., "Petroleum Hydrocarbon Mineralization in Anaerobic Laboratory Aquifer Columns," Journal of Contaminant Hydrology 32, pp. 41-61, 1998.

Ivanov, M. V. et al. "Additional Oil Production During Field Trials in Russia: Microbial Enhancement of Oil Recovery—Recent Advances" (4th US DOE MEOR Int Conf (Upton, NY, 1992) Proc; Elsevier Develop Petrol Sci Ser No. 39), 1993, pp. 373-381.

Ivanov, M. V. et al. "Die mikrobiologische Bildung von Methan in einer abzubauenden Erdollagerstatte" Frieberger Forschungshefte Reihe C, v., 1982, vol. 389, pp. 189-199.

Johnson et al., 1991, "Preliminary Results of a Coalbed Methane Assessment of the Wind River Indian Reservation, Whoming" Coalbed Methane, pp. 273-284.

Johnson, Ronald C. et al. "A Preliminary Evaluation of Coalbed Methane Resources of the Wind River Indian Reservation, Wyoming" Coal-Bed Methane Potential of the Wind River Indian Reservation, Ed. Stephen Manydeeds, Dec. 1991, pp. 40-64, Bureau of Indian Affairs Division of Energy and Mineral Resources.

Kasting, James F. "When Methane Made Climate" Scientific American, Jul. 2004, pp. 80-85.

Kim, Ann G. "Experimental Studies on the Origin and Accumulation of Coalbed Gas" U.S. Dept. of the Interior Bureau of Mines, Report of Investigations 8317, 1978, 18 pages.

Kim, Ann G. et al. "Hydrocarbon Gases Produced in a Simulated Swamp Environment" U.S. Dept. of the Interior Bureau of Mines, Report of Investigations 7690, 1972, 13 pages.

Klein, A. et al. "Comparative Analysis of Genes Encoding Methyl Coenzyme M Reductase in Methanogenic Bacteria", Mol Gen Genet, 1988, 213:409-420.

Krumholtz, Lee R. et al. "Confined subsurface microbial communities in Cretaceous Rock" Nature (Mar. 6, 1997) pp. 64-66.

Kunzig, Robert "20,000 Microbes Under the Sea" Mar. 2004, pp. 32-41, vol. 25, No. 3.

Law, Ben E. et al "Coalbed Gas Accumulations in the Paleocene Fort Union Formation, Powder River Basin, Wyoming" Coalbed Methane—1991; Rocky Mountain Association of Geologists, pp. 179-190.

Le Blanc, Leonard, Artificial Recharge, Offshore, p. 10, Feb. 2000.

L'Haridon, S., Reysenbach, A.L., et al., Hot Subterranean Biosphere in a Continental Oil Reservoir, Nature, v. 377, pp. 223-224, Sep. 21, 1995.

Li, M. et al. "Advances in Simulated Tests of Biogas" Oil & Gas Geology, 1996, v. vol. 17, No. 2, pp. 117-122, with abstract.

Lollar, B. Sherwood et al. "Evidence for bacterially generated hydrocarbon gas in Canadian Shield and Fennoscandian Shield rocks" Geochemicaet Cosmochimica Acta vol. 57, pp. 5073-5085 (1993).

Lomans, Bart P. et al. "Isolation and Characterization of *Mehanomethylovorans hollandica* gen. nov., sp. nov., Isolated from Freshwater Sediment, a Methyltrophic Methanogen Able to Grow on Dimethyl Sulfide and Methanethiol." Applied and Env. Microbiology, Aug. 1999, p. 3641-3650, vol. 65.

Lovely, Derek R. "Deep Subsurface Microbial Processes" Reviews of Geophysics, 33, Aug. 3, 1995, pp. 365-381.

Magot, Michel et al. "Microbiology of Petroleum Reservoirs" Antonie van Leeuwenhoek, 2000, 77: 103-116.

Mattavelli, L. et al. "Deep Isotropic Light Methane in Northern Italy" Bacterial Gas, Ed. R. Vially, 1992, pp. 121-132.

McDonald, I.R. et al. "Molecular Ecological Analysis of Methanogens and Methanotrophs in Blanket Bog Peat" Microbial Ecology (1999) 38:225-233.

Nandi, R et al. "Microbial Production of Hydrogen: An Overview" Critical Reviews in Microbiology, 24 (1): 61-84 (1998).

Nazina, T. N. et al. "Occurrence and Geochemical Activity of Microorganisms in High-Temperature, Water-Flooded Oil Fields of Kazakhstan and Western Siberia" Geomicrobiology Journal, 1995, v. 13, pp. 181-192.

Nazina, T. N. et al. "Microbial Oil Transformation Processes Accompanied by Methane and Hydrogen-Sulfide Formation" Geomicrobiology Journal, 1985, vol. 4, No. 2, pp. 103-130.

Neue, Heinz-Ulrich "Methane Emission from Rice Fields", BioScience, 1993, pp. 466-473, vol. 43, No. 7, downloaded from http://www.ciesin.org/docs/004-032/004-032.html.

Ng, T. K., and Weimer, P. J., "Possible Nonanthropogenic Origin of Two Methanogenic Isolates from Oil-Producing Wells in the San Miguelito Field, Ventura County, California", Geomicrobiology Journal, 1989, v. 7, pp. 185-192.

O'Carroll, Christopher "The Pervasive Presence of Microbes" http://www/umassmag.com/Summer_2003/The_pervasive_presence_of_microbes_5_08.html, 2003, 3 pages.

Orphan et al., "Culture-Dependent and Culture-Independent Characterization of Microbial Assemblages Associated with High-Temperature Petroleum Reservoirs," American Society for Microbiology, pp. 700-711, 2000.

Panow, A. et al. "Mechanisms of Biologically-Mediated Methane Evolution from Black Coal", Fuel Processing Technology v. 52, pp. 115-125, 1997.

Pedersen, K. "Exploration of Deep Intraterrestial Microbial Life: Current Perspectives" FEMS Microbiology Letters 185 (2000) pp. 9-16.

Potter et al. "Artificial Recharge," Offshore, Feb. 2000, pp. 10.

Puri et al. "Enhanced Coalbed Methane Recovery" Proceedings 1990 SPE Annual Technical Conference and Exhibition Reservoir Engineering, Sep. 23-26, 1990, New Orleans, Louisiana, SPE 20732, 1990, pp. 193-202.

Reeve, John N. "Archaebacteria Then . . . Archaes Now (Are There Really No Archaeal Pathogens?)" Journal of Bacteriology, vol. 181, No. 12, Jun. 1999 pp. 3613-3617.

Revesz, K. et al. "Methane production and consumption monitored by stable H and C isotope ratios at a crude oil spill site, Bemidji, Minnesota" Applied Geochemistry, 1995, vol. 10, pp. 505-515.

Rice, Dudley D. "Controls, habitat, and resource potential of ancient bacterial gas", Bacterial Gas, Ed. Vially, R., 1992, pp. 91-118, Paris.

Rice, Dudley D. et al. "Characterization of coal-derived hydrocarbons and source-rock potential of coal beds, San Juan Basin, New Mexico and Colorado, U.S.A." International Journal of Coal. Geology, 1989, pp. 597-626, vol. 13.

Rice, Dudley D. et al. "Composition and Origins of Coalbed Gas" Hydrocarbons from Coal: American Association of Petroleum Geologists Studies in Geology #38, Eds. Law, B.E., and Rice, D.D., 1993, pp. 159-184.

Rice, Dudley D. et al. "Generation, Accumulation, and Resource Potential of Biogenic Gas" The American Association of Petroleum Geologists Bulletin, vol. 65, No. 1, Jan. 1981.

Rice, Dudley D. et al. "Identification and Significance of Coal-Bed Gas, San Juan Basin, Northwestern New Mexico and Southwestern Colorado" *Geology and Coal-Bed Methane Resources of the Northern San Juan Basin, Colorado and New Mexico*, Ed. J. Fassett, Coal-Bed Methane, San Juan Basin, 1988, pp. 51-59, Rocky Mountain Association of Geologists.

Rice, Dudley D. et al. "Nonassociated Gas Potential of San Juan Basin Considerable" Oil & Gas Journal, Aug. 1990, pp. 60-61, vol. 88, No. 33.

Ridgley, J.L. et al. "Re-Evaluation of the Shallow Biogenic Gas Accumulation, Northern Great Plains, USA—Is the Similar Gas Accumulation in Southeastern Alberta and Southwestern Saskatchewan a Good Analog?" Summary of Investigations (1999) vol. 1 pp. 64-78.

Rightmire, C.T. et al. "Coalbed Methane Resource", 1984, Coalbed methane resources of the United States, AAPG Studies in Geology #17, Tulsa, p. 1-B.

Rooney-Varga, Juliette N. et al. "Microbial Communities Associated with Anaerobic Benzene Degradation in a Petroleum-Contaminated Aquifer", Applied and Environmental Microbiology, v. 65, No. 7, pp. 3056-3063, Jul. 1999.

Rozanova, E.P. et al. "Distribution of Sulfate-Reducing Bacteria Utilizing Lactate and Fatty Acids in Anaerobic Ecotopes of Flooded Petroleum Reservoirs" Institute of Microbiology, Academy of Sciences of the USSR, Moscow. Translated from Mikrobiologiya, vol. 60, No. 2, pp. 360-367, Mar.-Apr. 1991.

Rozanova, E.P. et al. "Microbiological Processes in a High-Temperature Oil Field", Microbiology, v. 70, No. 1, pp. 102-110, 2000.

Schoell, Martin "Genetic Characteristics of Natural Gases" The American Association of Petroleum Geologists Bulletin, Dec. 1983, p. 2225-2238, vol. 67, No. 12.

Schoell, Martin et al. "Natural Sites of Bio-Conversion of CO2 and Hydrocarbons in the Subsurface: San Juan Basin and Michigan Basin" 2001 AAPG Annual Convention, Jun. 3-6, 2001, p. A180, abstract only.

Scott, A.R., Intergas'95, "Limitations and Benefits of Microbiallly Enhanced Coalbed Methane"; May 15-19, 1995-The University of Alabama Tuscaloosa, 10 pages, 1995.

Scott, Andrew R. "Composition and Origin of Coalbed Gases from Selected Basins in the United States" Proceedings of the 1993 International Coalbed Methane Symposium, University of Alabama/Tuscaloosa, May 17-21, 1993; pp. 207-222.

Scott, Andrew R. "Improving Coal Gas Recovery with Microbially Enhanced Coalbed Methane" in Coalbed Methane: Scientific, Environmental and Economic Evaluation; Eds. M. Mastaletcz, M. Glikson, and S. Golding, 1999, pp. 89-110, Kluwer Academic Publishers, Netherlands.

Scott, Andrew R. "Review of Key Hydrogeological Factors Affecting Coalbed Methane Producibility and Resource Assessment" Oklahoma Coalbed-Methane Workshop, 1999, pp. 12-36.

Scott, Andrew R. et al. "A New Energy Resource: Microbially Enhanced Gas Generation" 2001 AAPG Annual Convention, Jun. 3-6, 2001, p. A182, abstract only.

Scott, Andrew R. et al. "Composition, distribution, and origin of Fruitland Formation and Pictured Cliffs Sandstone gases, San Juan basin, Colorado and New Mexico", in S.D. Schwochow, D.K. Murray, and M.F. Fahy, eds., Coalbed methane of western North America: Denver, Rocky Mountain Association of Geologists, 1991, p. 93-108.

Scott, Andrew R. et al. "Limitations and Benefits of Microbially Enhanced Coalbed Methane" International Unconventional Gas Symposium (INTERGAS), May 15-19, 1995; pp. 423-432.

Scott, Andrew R. et al. "Microbially Enhanced Coalbed Methane: Limitations and Possible Benefits" AAPG Convention, 1995, p. 86A, abstract only.

Scott, Andrew R. et al. "Relation between basin hydrology and Fruitland gas composition, San Juan Basin, Colorado and New Mexico" Methane From Coal Seams Technology, Nov. 1991, pp. 10-18, vol. 9, No. 1.

Scott, Andrew R. et al. "Thermogenic and Secondary Biogenic Gases, San Juan Basin, Colorado and New Mexico—Implications for Coalbed Gas Producibility" AAPG Bulletin, Aug. 1994, v. 78, No. 8, pp. 1186-1209.

Smith, John W. et al. "Microbial Origin of Australian Coalbed Methane" AAPG Bulletin, vol. 80, No. 6 (Jun. 1996), pp. 891-897.

Smith, John W. et al. "The Stable Isotope Geochemistry of Australian Coals" Org. Geochem. vol. 3, 1982, pp. 111-131.

Springer, E. et al. "Partial Gene Sequences for the A Subunit of Methyl-Coenzyme M Reductase (Mcrl) as a Phylogenetic Tool for the Family Methanosarcinaceae", International Journal of Systematic Bacteriology, 1995, pp. 554-559.

Takashima, M. et al. "Mineral Requirements for Methane Fermentation" Critical Reviews in Environmental Control, vol. 19, Issue 5 (1990) pp. 465-479.

Volkwein, J.C. et al. "Biological Production of Methane from Bituminous Coal", Fuel Processing Technology, v. 40, pp. 339-345, 1994.

Weiner, J. M., and Lovley, D. R. "Rapid Benzene Degradation in Methanogenic Sediments from a Petroleum-Contaminated Aquifer", Appl. Environ. Microbiology 1998, vol. 64, No. 5, pp. 1937-1939.

Wellsbury, Peter et al. "Deep Marine biosphere fuelled by increasing organic matter availability during burial and heating" Nature 388, 573-576 (Aug. 7, 1997).

Whitfield, John "Origins of life: Born in a watery commune" Nature, (Feb. 19, 2004) pp. 674-676, vol. 427.

Whiticar, Michael J. "Correlation of natural gases with their sources" In: Magoon L. and W. Dow (eds.) The Petroleum System From Source to Trap, AAPG Spec. Publ. Memoir 60, 1994, Ch. 16, 261-83.

Whiticar, Michael J. et al. "Biogenic methane formation in marine and freshwater environments: CO2 reduction vs. acetate fermentation—Isotope evidence" Geochimica et Cosmochimica Acta, 1986, pp. 693-709, vol. 50, No. 5.

Zengler et al., "Methane Formation From Long-Chain Alkanes by Anaerobic Microorganisms," Nature, vol. 401, pp. 266-269, Sep. 16, 1999.

Zobell, C.E., "Bacterial Release of Oil From Sedimentary Materials," The Oil & Gas Journal, pp. 62-65, Aug. 2, 1947.

* cited by examiner

BIOGENIC FUEL GAS GENERATION IN GEOLOGIC HYDROCARBON DEPOSITS

CROSS REFERENCES TO RELATED APPLICATIONS

This application is a continuation of prior application Ser. No. 11/343,429, filed Jan. 30, 2006, which was a continuation-in-part of International Application PCT/US2005/015259, with an international filing date of May 3, 2005. This application is also related to International Application PCT/US2005/015188, with an international filing date of May 3, 2005. The entire contents of all these applications are hereby incorporated by this reference for all purposes.

FIELD OF THE INVENTION

The present invention relates to methods of rearranging the constituent population of a native consortium of microorganisms to stimulate the growth of consortium members that produce metabolic products such as hydrogen and methane. Rearranging the constituents of the consortium may include diluting the consortium microorganisms with formation water extracted and transported from the geologic formation. It may also include introducing amendments to the native consortium that causes a change in the distribution of metabolic pathways and/or population distributions of consortium members.

BACKGROUND OF THE INVENTION

The formation water present in subterranean geologic formations of oil, coal, and other carbonaceous materials is normally considered an obstacle to the recovery of materials from those formations. In coal mining, for example, formation water often has to be pumped out of the formation and into remote ponds to make the coal accessible to mining equipment. Similarly, formation water has to be separated from the crude oil extracted from a subterranean field and disposed of typically underground. The extraction, separation and disposal of the formation water add costs to recovery processes, and generate a by-product regarded as having little value.

Further investigation, however, has revealed that even extracted formation water can support active communities of microorganisms from the formation. The presence of these microorganism in the formation environment were known from previous recovery applications, such as microbially enhanced oil recovery (MEOR), where the microorganisms naturally generate surface active agents, such as glycolipids, that help release oil trapped in porous substrates. In MEOR applications, however, it was generally believed that the microorganisms were concentrated in a boundary layer between the oil and water phases. The bulk formation water was believed to be relatively unpopulated, because it lacked a hydrocarbon food source for the microorganisms. More recent studies have shown that robust populations of microorganisms do exist in the bulk formation water, and can even survive extraction from the geologic formation under proper conditions.

The general concept of enhancing production of biogenic methane from a carbonaceous formation has been suggested previously [Raabe, S., Denver Post, Nov. 17, 2004, p. 1C]. Volkwein, supra, reported isolating a methanogenic sediment from an abandoned coal mine into which sewage had been discharged for an unspecified time period. For mine cavities having a particular history, from a time where a nutrient source was present to a time where the nutrient source was absent, sediment could be collected which was alleged to be methanogenic in the presence of bituminous coal. No supporting data were disclosed. Scott, et al. Pub. No. US 200410033557 A1 (Feb. 19, 2004) generally describes introducing subsurface fractures in a deposit of coal, carbonaceous shale or organic-rich shale and injecting various modifications including a consortium of selected anaerobic biological microorganisms, nutrients, carbon dioxide and other substrates for in situ conversion of organic compounds in said formation into methane and other compounds. The disclosure does not specifically teach how to obtain "selected" bacterial consortia; however, the reference suggests that collection of bacteria from formation waters may result in collection of only a few species rather than a representative sample of bacterial consortia. No supporting data of methane generation were reported. Menger, et al. U.S. Pat. No. 4,845,034 described carrying out a biochemical reaction in a subterranean cavity formed in a salt formation, limestone cavity or other earthen rock or sandstone formation. A feedstock of finely-divided, hot-alkali-treated coal would be inoculated under controlled conditions with a culture of microorganisms including acid formers and methanogens to produce methane. No data reporting methane biosynthesis were reported.

The discovery of active populations of microorganisms in bulk formation water has come at a time when new applications are being envisioned for these microorganisms. For years, energy producers have seen evidence that materials like methane are being produced biogenically in formations, presumably by microorganisms metabolizing carbonaceous substrates. Until recently, these observations have been little more than an academic curiosity, as commercial production efforts have focused mainly on the recovery of coal, oil, and other fossil fuels. However, as supplies of easily recoverable natural gas and oil continue to dwindle, and interest grows using more environmentally friendly fuels like hydrogen and methane, biogenic production methods for producing these fuels are starting to receive increased attention.

Many studies report isolating and characterizing MO's in naturally-occurring waters including ground water. Pickup et al. [Pickup, R. W. et al. (2001) J. Confam. Hydrol. %:269-2841 reported a detailed study of MO's in an aquifer polluted by a plume of phenolic material emanated from a single known source. Water from the aquifer was sampled at several depths from two boreholes within the plume. Details of the sampling method were disclosed by Thornton et al. [Thornton, S. F. et al. (2001) J, Contam. Hydrol. %:233-2671. Water samples were filtered though 0.22 pm polycarbonate filters, assayed for total MO count by acridine orange staining and by counting colonies of culturable MO's. The number of culturable MO's was 1% or less of the total measured by acridine orange staining. The authors used a variety of techniques to assess numbers and activities of various MO classes and to evaluate differences that varied with sample depth and phenolic concentration. The presence of methanogens was revealed using polymerase chain reaction analyses to amplify known methanogen-specific sequences. Methane generation was not reported.

Various filtration techniques have been reported for collecting MO's from groundwater. Schulz-Makuch et al [Schulze-Makuch, D. et al. (2003) Ground Water Monitor. and Remed. a:68-751 compared the efficacy of filter packs containing surfactant-modified zeolite or iron oxide-coated sand for removing $E.\ coli$ and MS-2 virus from contaminated groundwater. The surfactant-modified zeolite removed both the bacteria and the virus, but the iron oxide-coated sand was ineffective. Lillis et al [Lillis, T. 0. et al. (2001) Lett. Appl.

Microbiol. 2:268-2721 compared membrane filters to collect MO's from groundwater. Recovery was measured by comparing colony counts of MO's cultured after filtration. Filters of pore size 0.45 pm recovered about 90% of the MO's; however, the remaining MO's were recovered only after filtration through 0.22 pm filters. Filtration can remove both viable and non-viable cells. Culture conditions may not be suitable for growing many, or even most of the filterable MO's. Kunicka-Goldfinger et al. (1 977) Acta Microbiol. Polonica 26: 199-205, reported that an agar plate method of counting colony forming units (cfu) accounted for only 20-25% of organisms counted by direct staining of MO's isolated by filtration from lake waters. A "semi-continuous" method of culturing cells on the filters, wherein the cells were periodically exposed to filtered lake water to re-supply natural nutrients and remove waste products yielded significantly higher numbers of culturable microorganisms.

Tangential filtration has been reported for isolation of proteins and microorganisms. U.S. patent application Ser. No. 10/703,150, published Jun. 24, 2004 disclosed concentrating a suspension of microalgae by passing the suspension through a tangential filtering device. EPA document 815-0-03-008, June 2003 provides extensive technical and performance data for membrane filtration, including tangential flow filtration, in water purification systems.

To date, most contributions to the art have emphasized nutritional amendments in situ, or culturing microorganisms prior to injection into a formation or introducing fractures in a formation. Techniques for isolating a methanogenic consortium and demonstrating methanogenesis from an isolated consortium remain as problems inadequately addressed in the prior art.

Unfortunately, the techniques and infrastructure that have been developed over the past century for energy production (e.g., oil and gas drilling, coal mining, etc.) may not be easily adaptable to commercial-scale, biogenic fuel production. Conventional methods and systems for extracting formation water from a subterranean formation have focused on getting the water out quickly, and at the lowest cost. Little consideration has been given to extracting the water in ways that preserve the microorganisms living in the water. Similarly, there has been little development of methods and systems to harness microbially active formation water for enhancing biogenic production of hydrogen, methane, and other metabolic products of the microbial digestion of carbonaceous substrates. Thus, there is a need for new methods and systems of extracting, treating, and transporting formation water within, between, and/or back into geologic formations, such that microbial activity in the water can be preserved and even enhanced.

New techniques are also needed for stimulating microorganisms to produce more biogenic gases. Native consortia of hydrocarbon consuming microorganisms usually include many different species that can employ many different metabolic pathways. If the environment of a consortium is changed in the right way, it may be possible to change the relative populations of the consortium members to favor more combustible gas production. It may also be possible to influence the preferred metabolic pathways of the consortium members to favor combustible gases as the metabolic end products. Thus, there is also a need for processes that can change a formation environment to stimulate a consortium of microorganisms to produce more combustible biogenic gases.

BRIEF SUMMARY OF THE INVENTION

Embodiments of the invention include methods for stimulating biogenic methane production from a carbonaceous substrate. Methane production according to the invention can be stimulated in situ in an underground formation of carbonaceous material, or in extracted carbonaceous material. By contacting the carbonaceous material with a methanogenic consortium, methane synthesis has been demonstrated to occur, even in the case of carbonaceous material which was formerly deemed unproductive. The methods do not depend on providing exogenous amendments, multiplying consortium MO's in culture, addition of substrates, or upon prior nutrient injection, structural modification of the formation, or prior chemical modification of the carbonaceous material, although such steps are not excluded.

Embodiments of the invention also include methods of preparing a concentrate of microorganisms ("MO1s" hereinafter) including a consortium of MO's, which methods may include the steps of, a) extracting anaerobic formation water containing said MO's from an underground carbonaceous formation, b) providing liquid transport means for transporting the water while maintaining an anaerobic state, c) providing collection means for collecting the MO's in an anaerobic state from the water, and d) transporting the water through the collection means. The MO's may be collected from the water by collecting the MO's in a concentrated form in the water from the collection means, where a concentrate of said MO's is prepared. MO's prepared according to the invention are essentially sediment-free.

Embodiments of the invention also relate to methods to stimulate biogenic production of a metabolite with enhanced hydrogen content. The methods may include the steps of forming an opening in a geologic formation to provide access to a consortium of microorganisms, and injecting water into the opening to disperse at least a portion of the consortium over a larger region of a hydrocarbon deposit. The method may also include measuring a change in the rate of production of the metabolite in the formation.

Embodiments of the invention may still further relate to pumping and extraction methods to stimulate the biogenic production of a metabolite with enhanced hydrogen content. The methods may include forming an opening in a geologic formation to provide access to a native consortium of microorganisms. The method may also include injecting a first portion of water into the opening to disperse at least a portion of the consortium over a larger region of a hydrocarbon deposit, extracting formation fluids from the geologic formation following the water injection, and injecting a second portion of the water into the opening after extraction. The methods may also include measuring a change in the rate of production of the combustible gas in the formation.

Embodiments of the invention may also further include methods to stimulate biogenic production of a metabolite with enhanced hydrogen content by changing the salinity level of water in a geologic formation. The methods may include measuring a salinity level of formation water in a geologic formation. The methods may also include forming an opening in the formation to provide access to a consortium of microorganisms, and injecting water into the opening to reduce the salinity level of the formation water in the formation. The methods may additionally include measuring a change in the rate of production of the metabolite in the formation.

Embodiments of the invention still further relate to processes for enhancing a consortium of microorganisms to make materials with enhanced hydrogen content from carbonaceous substrates in an anaerobic environment. The processes may include extracting formation water from a geologic formation, and removing at least a portion of an extractable material from the formation water to make amended formation water. This extractable material may include microorganisms that are filtered out of water. The processes may further include introducing the amended formation water to the carbonaceous material.

Embodiments of the invention may also relate to processes for increasing biogenic hydrocarbon production in a geologic formation containing a carbonaceous material. The processes may include extracting formation water from the formation, and removing at least a portion of one or more hydrocarbons from the formation water to make amended formation water. Microorganisms in water may also be filtered and/or sterilized to make the amended formation water. The processes may further include reintroducing the amended formation water to the geologic formation.

Embodiments of the invention may also further relate to processes for transporting formation water between geologic formations. The processes may include extracting the formation water from a first formation, and removing at least a portion of a hydrocarbon from the formation water to make amended formation water. Microorganisms in water may also be filtered and/or sterilized to make the amended formation water. The processes may also include transporting the amended formation water to a second geologic formation, and introducing the amended formation water to the carbonaceous material in the second geologic formation. Microorganisms may also be extracted from the first formation and introduced to the second formation with the amended formation water.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

DETAILED DESCRIPTION OF THE INVENTION

Figure 1:
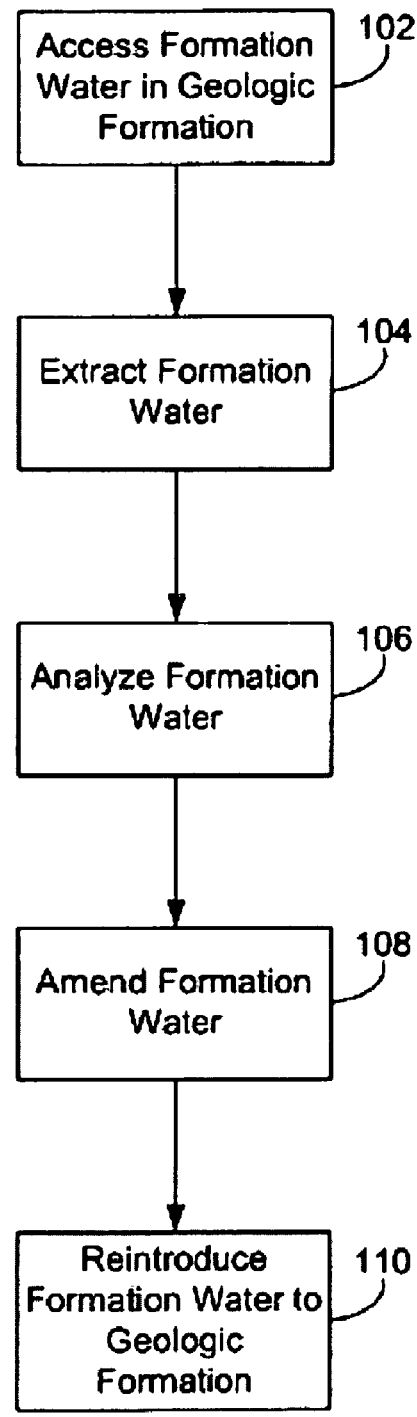
FIG. 1 is a flowchart illustrating a method of intraformation transport of formation water according to embodiments of the invention.

Methane is generated in a carbonaceous formation by metabolic activity of MO's within the formation. Typically, a plurality of MO species act to degrade complex hydrocarbons in the formation to metabolic precursors of methane such as to acetate and/or $CO_2$ which can be further metabolized to methane by various species of methanogens. The MO's whose concerted metabolic actions result in hydrocarbon degradation and methane production are termed a "methanogenic consortium" herein. Active MO's of a methanogenic consortium are likely to be most abundant in formation water of a methane-producing formation. Methods of preparing methanogenic consortium according to embodiments of the invention are now described.

I. Methods of Collecting, Preparing and Concentrating Methanogenic Constortium

The anaerobic state of formation water can be maintained during pumping, filtration and water storage by maintaining a closed system throughout and by injecting an inert gas such as argon, nitrogen or helium into the system to minimize contamination by oxygen. Preferred pumping means are low pressure pumps such as vein, fin or rotary pumps that use needle, ball or butterfly valves. Typically, pumps used for removing water from coal deposits are submersible. As is understood in the art, water pumped from a deep well releases dissolved methane and other gases as it is brought to the surface. Therefore, the use of submersible pumps combined with gas collection devices at the well-head are preferred by those skilled in the art. Preferred materials for transport and storage of anaerobic water are those which are oxygen impermeable and chemically inert, to minimize diffusion into the water of oxygen or other materials that could affect growth, viability or metabolic functions of MO's in the water. Examples of preferred materials include butyl rubber, viton, glass, steel and stainless steel. Examples of non-preferred materials include oxygen permeable tubing including nylon, tygon, silicone and polyvinyl chloride. The inventors have found that it is not possible to maintain anoxic conditions with these oxygen permeable materials.

It will be understood in the art that the choice of an optimal pumping device for a given formation will depend upon the volume of water to be processed, the depth of the anaerobic formation water source, temperature of the water, mineral content of the water, rate that water flow in the formation replaces the water removed, and the composition of the carbonaceous formation.

In general, pumps should be chosen that do not introduce air and do not create significant forces that could shear MO's.

All such features will be understood by those skilled in the art, taking into account the need to avoid oxygen intrusion into the water being pumped, and to maintain viability of MO's that exist in the water and therefore to avoid introducing physical or chemical factors that would compromise viability. It will be understood that pumping can occur in stages, using different pumping means for different stages. Monitoring devices can be used to assist in coordinating pumping rates and filtration rates, to regulate inert gas input as needed, measure oxygen concentration, cell concentration and trans-membrane pressure, and to measure water levels and head space volumes in any storage or holding tanks.

Examples of "liquid transport means," such as pumps, may include any device or combination of devices for transporting anaerobic formation water from one location to another. Pumping devices for withdrawing water from the formation and pressure devices for expelling water from the formation are contemplated. Pumping means can be operated mechanically, hydraulically, pneumatically or by fluid expansion. Pumping means include without limitation:

Any of the dynamic pumping devices described below:
centrifugal pumps, including axial flow [single-stage or multi-stage; closed impeller; open impeller (either fixed-pitch or variable-pitch); including any combination of these characteristics]; mixed flow and/or radial flow [single suction or double suction; self-priming, non-priming, single-stage, or multi-stage; open-impeller, semi-open impeller, or closedimpeller; including any combination of these characteristics]; and peripheral [single-stage or multi-stage; self-[priming or non-priming; including any combination of these characteristics];
jet pumps;
gas lift pumps;
hydraulic ram pumps;
electromagnetic pumps.

Any reciprocating displacement pumping device, as described below:
piston or plunger pumps, including steam [simplex, duplex, triplex or multiplex]; and power [single-acting or double-acting; simplex, duplex, triplex or multiplex; including any combination of these characteristics];
pumps utilizing check valves (whether fixed, mobile, or any combination of these characteristics) including hinged barriers, mobile balls or mobile pistons of appropriate shape, with associated containment devices;
diaphragm pumps, including simplex, duplex and multi-plex, fluidoperated and mechanically-operated, and including any combination of these characteristics.

Any rotary displacement pumping device, as described below:
pumps equipped with a single rotor, including vane, piston, flexible member, screw and peristaltic;
pumps equipped with multiple rotors, including gear, lobe, circumferential piston, and screw.

Microorganisms can be collected from aqueous fluids by a variety of means, including filtration, centrifugation, flocculation, affinity binding, and the like. Preferred collection means are filtration and centrifugation, since these do not depend on specific chemical or biochemical properties of the MO's in the fluid and they can be adapted to continuous flow for processing large volumes of fluid. Filtration is especially preferred because it is more readily adaptable to maintaining an anaerobic state. Filtration is the process of collecting, fractionating, or concentrating particles, molecules, or ions within or from a fluid by forcing the fluid material through a porous or semi-porous barrier. The force can be pressure differential, vacuum, concentration gradient, valence or electrochemical affinity. The fluid can be either liquid or gas. Two common types of filtration include:
 a. Dead-end (linear) filtration; and
 b. Tangential (cross) flow filtration.

Filters are generally of two types, either depth filters or membrane filters. Depth filters do not have absolute pore sizes, but trap some particles on the surface of the filter, some particles by random entrapment and adsorption within the filter, and possible particle retention through charge. Membrane filters generally function by retaining particles through an absolute pore size. Most MO's can be retained on filters having a maximum pore size of about 0.2 microns.

Factors that affect filtration rate include pore size, filter composition, density of MO's in the water and presence of contaminating particles. Particles other than MO's, that are too large to pass through the pores of a filter can clog the filter, particularly if present in excess of the MO's themselves. Particles larger than MO's can be removed prior to collecting the MO's by means known in the art, often by a pre-filtration process that does not significantly remove MO's from the water. Settling tanks can also be used for removing large particles. Filters having a maximum pore size less than 0.2 microns have reduced flow rate and are less preferred.

Filter materials will be chosen to provide optimum pore size and hydrophobicity. While MO's are more easily removed from hydrophobic filter materials, the flow rate of water through a filter membrane is lower for highly hydrophobic membranes. Flow rate is also reduced as pore size is reduced. Filters having nominal pore size of 0.45 microns will retain most MO's. However, a significant number of small MO's have been reported in ground-water samples [see, e.g. Lillis, et all supra]. Preferred filters will have pore sizes of about 0.2-0.45 microns and preferably be composed of polyether sulfones, polysulfones, cellulose acetate or PVDF. Filters composed of nylon or nitrocellulose are not preferred.

Efficient processing of large water volumes can be achieved by increasing filter area. The optimum filter area to be employed will depend on the volume to be processed and the desired rate of processing. Various configurations for maximizing filter area within a given sized device are known in the art. A common configuration is a pleated sheet rolled into a cylinder. Another common configuration is a flat sheet rolled into a spiral around a cylindrical core. Other configurations are known in the art and can be adapted for use in the present invention by those skilled in the art. Tangential, or cross-flow filtration is an effective expedient for filtering large volumes of water. Suitable filters available commercially having the described characteristics are polyether sulfone hollow fiber filters having 0.2 microns nominal pore size. For laboratory scale filtrations, filters having 2000 $cm^2$ surface area, such as Spectrum Technologies part no. M22M-301-01N have been successfully employed. For large scale processing, modules of Spectrum Technologies M22M-600-01 N with a 5200 $cm^2$ surface area can be linked in parallel. The foregoing are provided as non-limiting examples. Other filter types and filter materials are known to those of skill in the art.

During tangential flow filtration, water is removed from fluids that are recirculated through a tangential flow filter. This yields water (often termed retentate) that is concentrated with microorganisms. The retentate can be pumped into a storage tank that has been sparged with an inert gas, after which the tangential flow filtration of additional water can resume. Microorganisms can also be removed from filter means by washing or backwashing, to provide the MO's at higher concentration than in the formation water. If desired, further concentration can be achieved by additional rounds of filtration. In addition, MO's obtained in a semi-concentrated form by filtration can be further concentrated by centrifugation or dehydration to yield a paste or slurry of packed or highly concentrated cells. By application of such processes, formation water having relatively low biomass, as little as $10^2$ cell/ml can be processed to yield MO's at concentrations of $10^8$/ml or more. Transporting anaerobic formation water through such separation means, whether in single or plural stages, whether by use of one or more of such means in tandem, all while maintaining an anaerobic state, can yield viable, active methanogenic consortia present in the formation water in a concentrated form. Anaerobic formation water from which viable methanogenic consortia were isolated was clear to the naked eye. Nevertheless, it will be understood that small particles of organic or inorganic matter may be retained along with MO's in the course of filtration and centrifugation carried out as described herein. Microscopic analysis of MO concentrates prepared according to the invention revealed numerous discrete rodshaped cells and few if any irregular particles or particles with cells attached. The term "essentially sediment-free" is used to denote a preparation of cells that contains at least 50% discrete or clustered cells, unattached to debris or non-cellular particles. Cell viability can be evaluated by methods known in the art, for example by assessing all membrane integrity based on permeability to a cell permeant DNA-binding fluorescent dye.

The inventors herein have made the surprising discovery that all the MO species that make up a methanogenic consortium capable of generating methane from the carbonaceous matter in their formation of origin, can be recovered in a viable, active state from formation water, under anaerobic conditions. Formation water is abundant. The present invention provides abundant consortium MO's by simple, inexpensive means, and without the use of expensive fermentation processes. The consortia MO's in concentrated form, are useful for inoculating carbonaceous materials, in situ or above ground, to generate methane or to amplify the generation of methane using the carbonaceous materials as substrate. The consortia have been demonstrated herein to stimulate methanogenesis from essentially non-productive coal, without prior analysis of individual strains or their nutritional requirements, without added nutrients and without growing the cells in culture prior to contacting the coal with consortium MO's.

II. Methods of Changing Consortium Makeup with Water Additions

Methods of stimulating the production of biogenic metabolites with enhanced hydrogen content (e.g., combustible gases such as methane and hydrogen) by changing the makeup of a consortium of microorganisms are described. The changes may be brought about by diluting a native consortium in water to disperse consortium members over a larger region of a geologic formation. The dispersion can create opportunities for the microorganism to grow with less competition from consortium members that do not generate metabolites with enhanced hydrogen content. When the microorganisms are spread out over a larger region of a carbonaceous substrate (e.g., a hydrocarbon deposit such as an oil or coal bed) the microorganism that are most effective at utilizing the substrate as a food source are expected to grow at the fastest rates. In an anaerobic formation environment, those metabolic processes typically include the conversion of the substrate to biogenic gases such as hydrogen and methane, among other gases, as well as acetate (e.g., acetic acid). Consequently, the dispersion of the consortium in water is expected to increase population growth for those microorganism species that are more efficient at converting hydrocarbon substrates into metabolic products having enhanced hydrogen content such as hydrogen and methane.

While the aqueous dispersion may favor the growth of the hydrocarbon metabolizers over other consortium members, it may not have as great an impact on the favored metabolic pathways of the metabolizers. For example, a methanogenic microorganism may be able to convert the hydrocarbon substrate into either methane or acetate. Embodiments of the invention also include methods of stressing the microorganism to favor metabolic pathways that produce a target metabolic product (e.g., hydrogen, methane, etc.) over other products (e.g., acetate, ammonia, hydrogen sulfide, carbon dioxide etc.). These methods include introducing an amendment to the formation environment surrounding the microorganism consortium that may have an effect on the metabolic pathways at least some of the consortium members favor. The amendment may include a metabolite (i.e., a chemical intermediary or product of a metabolic process) generated by some of the consortium members. By concentrating the consortium environment with the metabolite, the consortium members may be influenced to favor a different metabolic pathway that does not produce even more of the metabolite. Alternatively, a rate limiting metabolite may be introduced that normally causes a bottleneck in a metabolic pathway. Introducing this amendment to the consortium environment may stimulate more use of the pathway to consume the added metabolite.

The water used for the dilution and dispersion of the consortium may come from a variety of sources. One source that may be in close proximity to the formation is formation water. Systems and methods for the transport of anaerobic formation water from a subterranean geologic formation are described. "Anaerobic" formation water is characterized as having little or no dissolved oxygen, in general no more than 4 mg/L, preferably less than 2 mg/L, most preferably less than 0.1 mg/L, as measured at 20 degrees C. and 760 mmHg barometric pressure. During application of the present invention, higher levels of dissolved oxygen, greater than 4 mg/L, can be tolerated without appreciably degrading microorganism performance, for limited times or in certain locations such as a surface layer in a storage or settling tank. Dissolved oxygen can be measured by well-known methods, such as by commercially-available oxygen electrodes, or by the well-known Winkler reaction.

The formation water may be extracted and then reintroduced into the same formation in an intraformation transport process, or introduced into a different formation in an interformation transport process. The formation water may be analyzed to determine the chemical composition of the water, and to ascertain whether microorganisms are present. When microorganisms are present, they may also be identified by genus and/or species.

The choice of formation water may be influenced by the content and/or activity of the microorganism found in the water. For example, a first formation having native formation water containing high concentrations of a microorganism of interest may be transported to a second formation to attempt to stimulate the growth of the microorganism in the second formation. The water transported to the new formation may contain a population of the microorganism, which may act as a seed population for the growth of the microorganism in the second formation.

The formation water may be amended based on the analysis of the compounds and microorganisms present in the native water. These amendments may include changing the composition of the formation water to enhance the growth of one or more species of the microorganisms present. For example, the amendments may include adjusting the microorganism nutrient levels, pH, salinity, oxidation potential (Eh), and/or metal ion concentrations, among other compositional changes to the formation water. The amendments may also include filtering and/or processing the formation water to reduce the concentration of one or more chemical and/or biological species.

Amended or unamended, the extracted formation water is transported back to the same formation, or a different formation. For example, intraformation transport may include cycling the formation water through the formation one or more times, where the water may be extracted from the formation, amended, and returned to the formation in a continuous loop process. Interformation transport may include, for example, extracting formation water from a first formation and transporting it (treated or untreated) to a second subterranean formation that has carbonaceous materials, but little or no native formation water and/or microorganisms. The aqueous environment introduced to the second formation creates conditions for microorganism populations to grow and convert the carbonaceous material into hydrogen, smaller hydrocarbons (e.g., butane, propane, methane), and other useful metabolites.

Referring now to FIG. 1, a flowchart is shown that illustrates a method of intraformation transport of formation water according to embodiments of the invention. The method starts with the accessing the formation water 102 in a geologic formation. The geologic formation may be a previously explored, carbonaceous material containing, subterranean formation, such as a coal mine, oil field, natural gas deposit, carbonaceous shale, etc. In many of these instances, access to the formation water can involve utilizing previously mined or drilled access points to the formation. For unexplored formations, accessing the formation water may involve digging, or drilling through a surface layer to access the underlying water.

Once the formation water is accessed, it may be extracted from the formation 104. The extraction may involve bringing the formation water to the surface using one or more hydrologic pumping techniques. These techniques may include pumping the formation water to the surface using a pumping device that harnesses electrical, mechanical, hydraulic, pneumatic, and/or fluid-expansion type forces, among other modes of action.

The extracted formation water may be analyzed 106 to ascertain information about the chemical and biological composition of the water. Chemical analyses may include spectrophotometry, NMR, HPLC, gas chromatography, mass spectrometry, voltammetry, and other instrumentation and chemical tests. The tests may determine the presence and concentrations of elements like carbon, phosphorous, nitrogen, sulfur, magnesium, manganese, iron, calcium, zinc, tungsten, and titanium, among others. The tests may also detect the presence and concentrations of polyatomic ions, such as $PO_4^{2-}$, $NH_4^+$, $NO_2^-$, $NO_3^-$, and $SO_4^-$, among others. Biological analyses may include techniques and instrumentation for detecting genera and/or species of one or more microorganisms present in the formation water. These test may include genus and/or species identification of anaerobes, aerobes, microaerophiles, etc. found in the formation water. Additional details for identifying and isolation genera and species of microorganisms from the formation water are described in commonly assigned U.S. patent application Ser. No. 11/099,879, filed Apr. 5, 2005, and titled "Systems and Methods for the Isolation and Identification of Microorganisms from Hydrocarbon Deposits", the entire contents of which are hereby incorporated by reference for all purposes.

The formation water may also be amended 108 by, for example, altering one or more physical (e.g., temperature), chemical, or biological characteristics of the water. As noted above, the amendments may include adjustments to the chemical composition of the formation water, including the increase or decrease of a microorganism nutrient level, pH, salinity, oxidation potential (Eh), and/or metal ion concentration, among other chemical species. For example, changes in microorganism nutrient levels may include changes in formation water concentration of cationic species, such as ammonium, calcium, magnesium, sodium, potassium, iron, manganese, zinc, and copper, among other cationic species. It may also include changes in anionic species, such as nitrate, nitrite, chloride, carbonate, phosphate, acetate, and molybdate, among other anionic species. It may further include changes in the nutrient level of compounds including disodium hydrogen phosphate, boric acid, yeast extract, peptone, and chelating compounds like nitrilotriacetic acid, among other compounds.

Changes in the biological characteristics of the formation water may include increasing or decreasing the population of one or more genera and/or species of microorganism in the water. Genera whose population in the formation water may be controlled include, *Thermotoga, Pseudomonas, Gelria, Clostridia, Moorella, Thermoacetogenium, Methanobacter, Bacillus, Geobacillus, Methanosarcina, Methanocorpusculum, Methanobrevibacter, Methanothermobacter, Methanolobus, Methanohalophilus, Methanococcoides, Methanosalsus, Methanosphaera, Granulicatella, Acinetobacter, Fervidobacterium, Anaerobaculum, Ralstonia, Sulfurospirullum, Acidovorax, Rikenella, Thermoanaeromonas, Desulfovibrio, Dechloromonas, Acetogenium, Desulfuromonas, Ferribacter*, and *Thiobacillus*, among others. Additional description of microorganisms, and consortia of microorganisms, that may be present and controlled in the formation water can be found in commonly assigned U.S. patent application Ser. No. 11/099,881, filed Apr. 5, 2005, and titled "Generation of materials with Enhanced Hydrogen Content from Anaerobic Microbial Consortia"; and U.S. patent application Ser. No. 11/099,880, also filed Apr. 5, 2005, titled "Generation of Materials with Enhanced Hydrogen Content from Microbial Consortia Including Thermotoga", the entire contents of both applications hereby being incorporated by reference for all purposes.

Whether amended or not, the extracted formation water may be reintroduced back into the geologic formation 110. The formation water may be reintroduced at or near the location where the water is extracted, or at a position remote from the extraction location. The remote position may or may not be in fluid communication with the extraction location (e.g., a cavity in the formation that is hydraulically sealed from the point where the formation water is extracted).

The formation water may be maintained in an anaerobic state during the extraction, pumping, transport, storage, etc., by using a closed system throughout and displacing the oxygen present in the system with an inert gas, such as argon, substantially pure nitrogen, and/or helium, among other inert gases. The system may also be pressurized with the inert gas to reduce the amount of ambient oxygen that enters the system. Embodiments of anaerobic formation water extraction, transport and storage systems may include low pressure pumps (e.g., vein, fin, and/or rotary pumps, which may use needle, ball and/or butterfly valves) that may be submersible in the subterranean formation water deposit. The conduits and storage elements of the system may be made of oxygen impermeable and chemically inert materials that minimize the diffusion of free oxygen and other contaminants into the anaerobic formation water. Examples of these materials may include butyl rubber, viton, glass, copper, steel, and stainless steel, among other materials.

Figure 2:
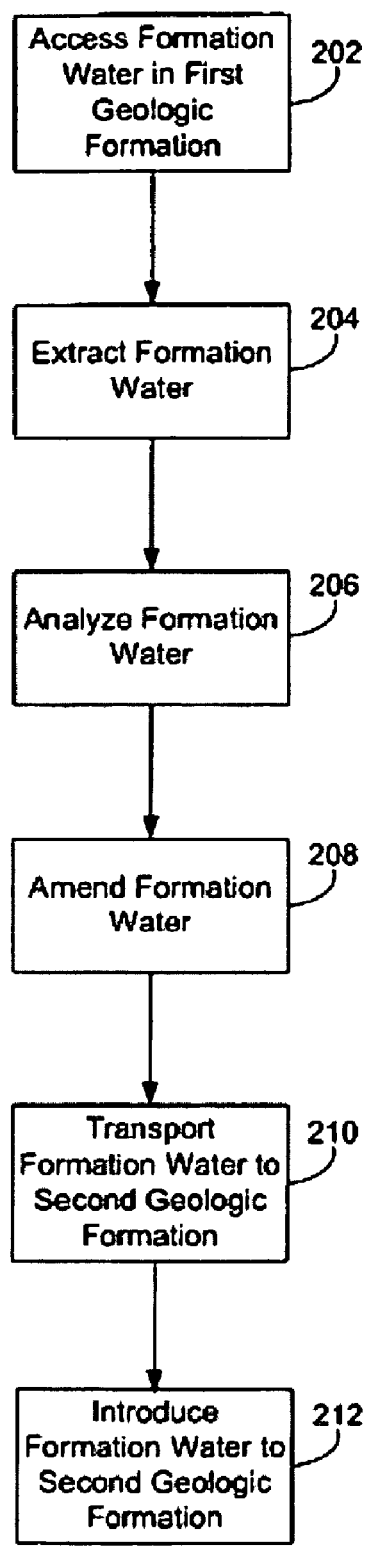
FIG. 2 is a flowchart illustrating a method of transporting of formation water between formations (i.e., interformation transport) according to embodiments of the invention.

FIG. 2 shows another flowchart illustrating a method of interformation transport of formation water according to embodiments of the invention. Similar to embodiments of methods of intraformation transport shown in FIG. 1, interformation transport may include accessing the formation water 202 in a first geologic formation, and extracting the water 204 from the first formation. The extracted formation water may be analyzed 206, and amended 208 by altering one or more physical, chemical, and/or biological characteristics of the water.

The formation water may then be transported to a second geologic formation 210. A variety of mechanisms are contemplated for transporting the formation water between the two geologic formations. These include pumping the water through a pipeline that is in fluid communication between the formations. They also include filling containers (e.g., barrels) with formation water and transporting them by vehicle (e.g., car, truck, rail car) to the second formation site. Alternatively, a vehicle designed for the transport of fluids (e.g., a tanker truck, tanker rail car, etc.) may be filled with the formation water at the first formation site and driven (or pulled) to the second formation site.

When the formation water arrives at the second formation site, it is introduced into the second geologic formation 212. The second geologic formation may be a dry formation, where the formation water is pumped into a cavity, network of channels, etc. having little or no detectable levels of native formation water. Alternatively, substantial amounts of native formation water may be present in the second formation, and the water from the first formation is mixed with this native water as it is introduced into the second formation.

Figure 3:
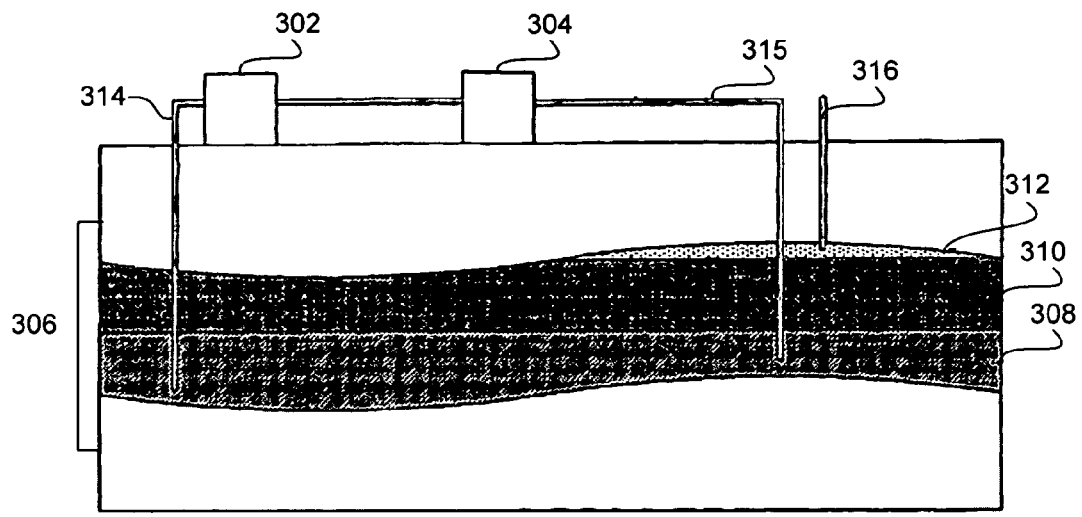
FIG. 3 shows a system for the transporting of formation water within a formation (i.e., intraformation transport) according to embodiments of the invention.

FIG. 3 shows a system 300 for intraformation transport of formation water according to embodiments of the invention. The system 300 may include a pump system 302 and amendment system 304 that are positioned on the surface above a subterranean geologic formation 306. The geologic formation 306 may include a formation water stratum 308 that sits below a liquid hydrocarbon layer 310 (e.g., a crude oil containing stratum), which, in turn, may sit below a gas layer 312 (e.g., a natural gas layer). A conduit 314 may be inserted into the formation and positioned such that a distal end of the conduit 314 receives formation water from the stratum 308 and transports it to pump 302 on the surface. In some examples, the conduit 314 may be part of a previous system used to recover hydrocarbons for the formation.

The pump system 302 used to bring the formation water to the surface may include one or more pumping devices such as dynamic pumping devices, reciprocating displacement pumping devices, and rotary displacement pumping devices, among others.

Dynamic pumping devices may include centrifugal pumps, such as axial flow centrifugal pumps, mixed flow and/or radial flow pumps, peripheral pumps, and combinations of these pumps. Axial flow pumps may include single-stage or multi-stage, closed impeller, open impeller (e.g., fixed-pitch or variable-pitch) and combinations of these pumps. Mixed flow and/or radial flow centrifugal pumps may include single suction or double suction, self-priming, non-priming, single-stage, or multi-stage, open-impeller, semio-pen-impeller, closed-impeller, and combinations of these types of pumps. Peripheral centrifugal pumps may include single-stage or multi-stage, self-priming or non-priming, and combinations of these types of pumps. Dynamic pumps may also include jet pumps, gas lift pumps, hydraulic ram pumps, and electromagnetic pumps, among other types of dynamic pumps.

Reciprocating displacement pumping devices may include piston or plunger pumps, including steam pumps (e.g., simplex, duplex, triplex or multiplex steam pumps). These pumps may also include power pumps (e.g., single-acting or double-acting; simplex, duplex, triplex, multiplex, and combinations of these power pumps). Also included are pumps utilizing check valves, whether fixed, mobile, or a combination of these characteristics, and may further include hinged barriers, mobile balls or mobile pistons of appropriate shape, with associated containment devices. Also included in reciprocating displacement pumping devices are diaphragm pumps, including simplex, duplex and multiplex, fluid-operated, mechanically-operated, and combinations of these type of pumps.

Rotary displacement pumping devices include pumps equipped with a single rotor, including vane, piston, flexible member, screw and peristaltic pumps. These pumps may also include pumps equipped with multiple rotors, including gear, lobe, circumferential piston, and screw pumps.

At least part of the pump system 302 may be submerged in a pool of formation water in a subterranean formation. In operation, the submerged pump may agitate the formation water, causing dissolved methane and other gases to be released and rise to the top of the formation. Thus, in some embodiments the pump system 302 may include a gas collection system (not shown) at the well head to transport the released gases out of the formation.

When formation water exits the pump system 302 it may be transported to an amendment system 304 where the water may be analyzed and/or amended before being reintroduced back into the formation 306. The analysis components of the system 304 may include chemical and biological measurement instrumentation (not shown) used to provide data on the chemical and biological composition of the formation water. The system 304 may also include components and equipment to change the physical, chemical and biological composition of the formation water. For example, the system 304 may include components to increase or decrease the temperature of the water. The system may also include components and equipment to filter the formation water to remove selected chemical and/or biological species. Descriptions of systems and method for filtering formation water can be found in co-assigned PCT Patent Application No. PCT/US2005/015188, filed May 3, 2005, and titled "Methanogenesis Stimulated by Isolated Anaerobic Consortia", the entire contents of which is hereby incorporated reference for all purposes. The amendment system 304 may also include components for increasing or decreasing a microorganism nutrient level, pH, salinity, oxidation potential (Eh), and/or metal ion concentration, among other chemical changes to the water.

Formation water passing through the pump system 302 and the amendment system 304 may then be transported thorough the pipeline 315 back into the formation 306. In the embodiment shown, the formation water is reintroduced into the same formation water layer 308, but at a different point from where the water was originally extracted. Alternatively, the formation water may be introduced back into the formation at another layer, such as where an end of the conduit 316 opens to the gas layer 312.

Figure 4:
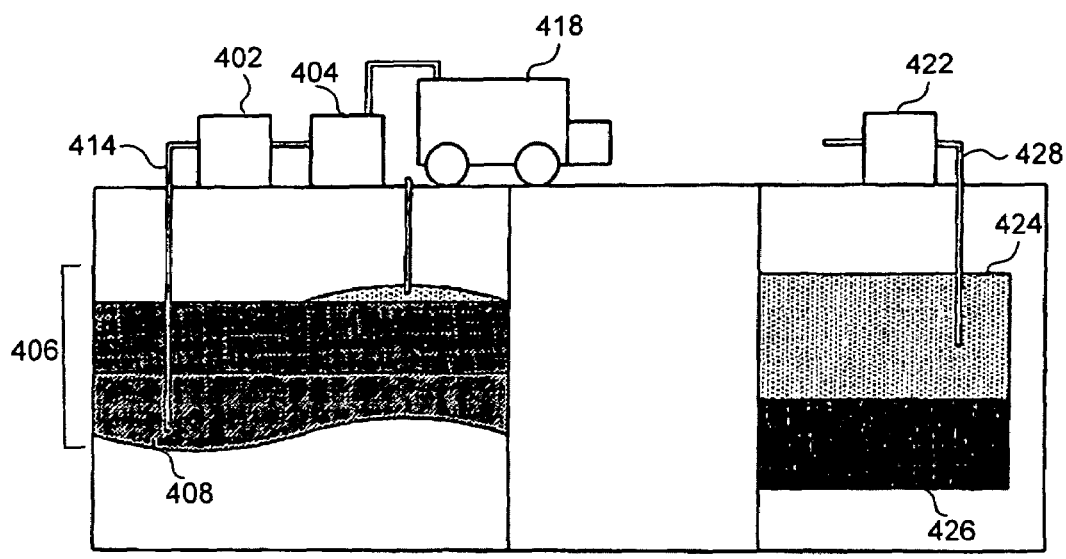
FIG. 4 shows a system for interformation transport of formation water according to embodiments of the invention.

Referring now to FIG. 4, a system 400 for interformation transport of formation water according to embodiments of the invention is shown. The System 400 include a pump system 402 and an amendment system 404 positioned above a first geologic formation 406. Formation water may be extracted by pump system 402 from a formation water layer 408 through the conduit 414, and analyzed and amended in amendment system 404. The amended formation water may then be loaded into the vehicle 418 which can travel between the first formation 406 and the second geologic formation 420.

When the vehicle 418 is filled with formation water it can travel to pumping system 422 positioned above the second formation 420. An outlet (not shown) on the vehicle 418 may be connected to the pump unit 422 and the formation water may be delivered to a subterranean cavity 424 above a hydrocarbon bed 426, in the second formation 420, via conduit 428. In alternative embodiments (not shown) the vehicle 418 may include pumping equipment on-board to pump the formation water into the cavity 424, without the use of an on-site pumping system 422. In more alternative embodiments, the vehicle 418 may be replaced by a transport pipeline (not shown) that transports the formation water directly between the first and second formations 408 and 420.

The extracted formation water may be used to disperse the constituents of a native consortium over a larger region of carbonaceous material. The aqueous dispersion provides an opportunity for the upstream metabolizers (e.g., the "first-bite" microorganisms that metabolize the hydrocarbon substrate into smaller molecules) and methanogenic microorganisms in the consortium to grow with less interference from nearby competing species that are flushed from the hydrocarbon deposit. When conditions in the formation environment are favorable to rapid growth of the dispersed upstream metabolizers and methanogens, the relative populations of species in the consortium may become more weighted to these consortium populations. Thus, diluting an original consortium (e.g., a native consortium) with water may change the demographics of the microorganism members to increase the production of biogenic gases such as methane and hydrogen.

Figure 5A:
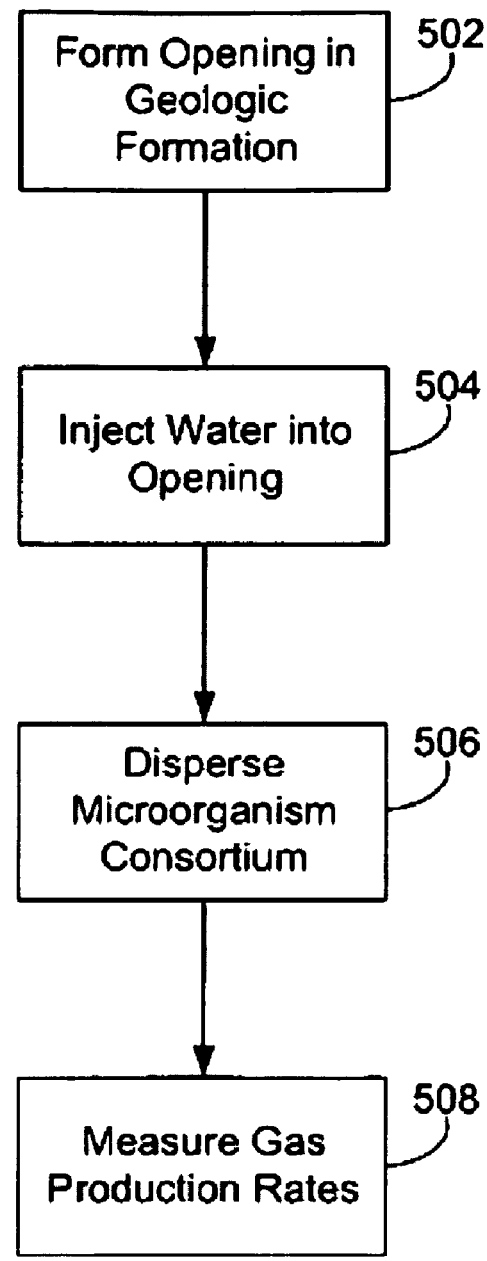
FIGS. 5A-B are flowcharts illustrating methods according to embodiments of the invention of using water to stimulate biogenic gas production by a consortium of microorganisms.
Figure 5B:
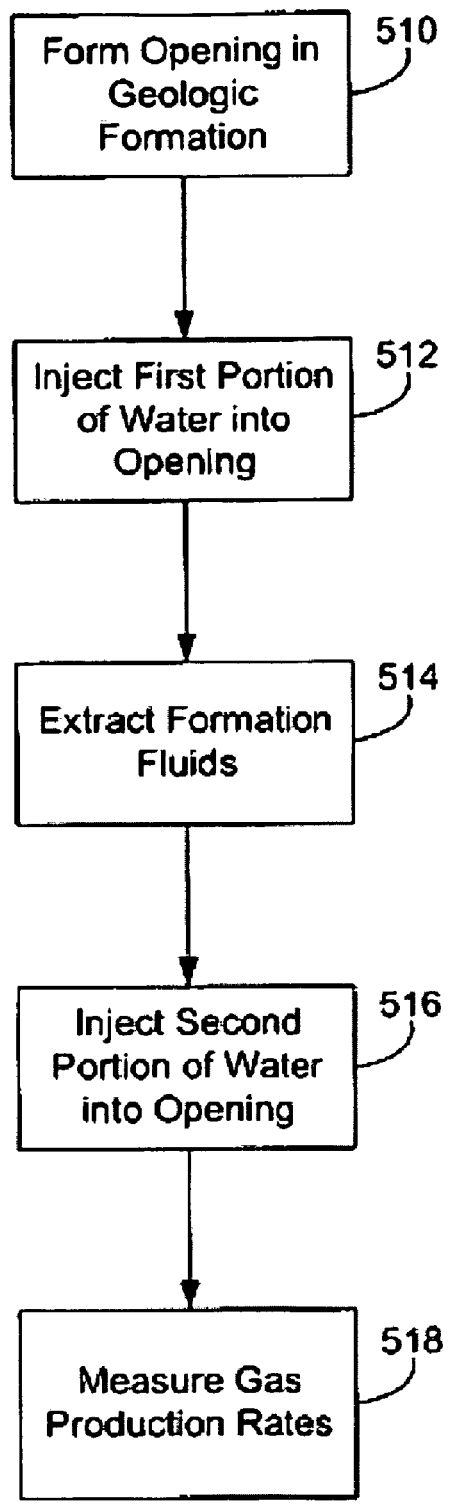

FIGS. 5A-B show flowcharts that illustrate methods of using water to stimulate biogenic gas production by a consortium of microorganisms. The method steps illustrated in FIG. 5A include forming an opening in a geologic formation 502 so water can be supplied to the microorganism consortium. The opening may be formed under conditions that limit the amount of atmospheric oxygen that flows into the opening. Formation of the opening may include boring, drilling, digging, blasting, excavating, etc., the opening starting at the surface of the formation. Embodiments also include unplugging or otherwise accessing a opening that has already been formed in the formation (e.g., a previously drilled oil well).

Following the formation of the opening, water may be injected into the opening 504. The water may have been extracted from the same formation, or have come from a different source, for example a different formation. The injected water may include live microorganisms, or the water may be treated to remove or inactivate the microorganisms. Removal treatments may include passing the water through a filter that collects the microorganisms in the retentate. Inactivation treatments may include heating and/or irradiating the water to kill the microorganisms present. Inactivation treatments may also include adding a biocide to the water to kill the microorganisms.

The water injected into the opening may disperse the consortium of microorganisms over a larger region of the formation 506. For example, if the consortium is concentrated in a specific region of a hydrocarbon deposit (e.g., a coal or oil deposit), the water may disperse the consortium over a larger region of the same deposit. The water may also dilute the consortium in a larger volume of fluid.

The rate of gas production may be measured 508 to determine the effect of injecting the water. Measured gases may include hydrogen, methane, carbon monoxide, and/or carbon dioxide, among other gases. The type of measurement may include a pressure measurement of the gases in the formation. This may involve partial pressure measurements of a particular gas (or group of gases), like the combustible gases methane and/or hydrogen. Measurements may be done before the water injection to establish a baseline rate of off-gassing in the formation. Additional measurements may be taken after the water injection to observe if the rate of gas production has changed as a result of the injection.

The water injection may be as simple as injecting a single sample into the opening. Embodiments may also include more complex patterns of water injection, where multiple cycles of water injection and extraction of fluids from the formation are performed. FIG. 5B shows a water injection pattern that includes the injection of two portions of water between an extraction step. Similar to FIG. 5A, the method may include forming an opening in a geologic formation 510 and injecting a first portion of water into the opening 512. A vacuum or some other type pressure differential may be applied to the opening to extract formation fluids from the opening 514. Following the extraction, a second portion of water may be injected into the opening 516. Measurement of the gas production rates 518 may be taken before, during and after the water injection cycle to determine how the injected water is affecting gas production rates in the formation.

It should be appreciated that the injection-extraction-injection cycle shown in FIG. 5B may include more iterations. It should also be appreciated that the volume of the water injected and the timing of the injection may be varied. For example, a first injection pattern may involve several injection cycles of smaller volumes of water, while a second pattern may involve fewer injection cycles of larger volumes of water.

Figure 6A:
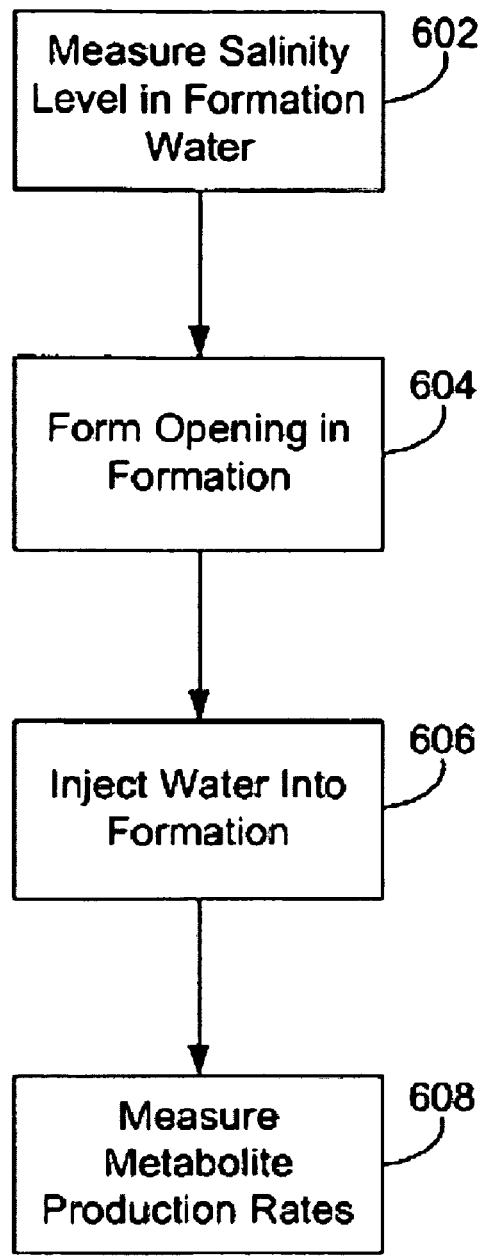
FIGS. 6A-B are flowcharts illustrating methods according to embodiments of the invention of controlling the salinity level of the water in a geologic formation.

Water injections and water treatments may also be done to change the salinity level of water in geologic formation. FIG. 6A shows steps in methods of controlling the salinity level of the water in a geologic formation according to embodiments of the invention. The methods may include measuring the salinity level in the formation water 602. If the salinity of the water is about 6% salt, by volume, or more (e.g., brackish or saline water) then some microorganisms in the formation environment may have reduced activity due to the high salt concentration. When the measured salinity level is high enough to interfere with the desired microorganism activity, an opening may be formed in the formation 604 that provides access for a water dilution amendment. Water having a reduced salinity level may be injected into the formation 608 through the opening. During the water injection, the salinity level of the in situ formation water may be monitored to quantify the impact of the water dilution. The salinity level in the formation water may continue to be monitored after the water injection to see if the salinity level starts to rise again. Measurements of metabolite production rates, such as production rates for hydrogen, methane, carbon monoxide, acetate, etc., may also be conducted 608 to gauge the impact of the reduced salinity level on biogenic activity.

The desired salinity level in a geologic formation depends in part on the microorganism consortium. Some native or introduced consortia are more active metabolizing carbonaceous substrates to metabolites with increased hydrogen content when the salinity level is about 6% or less. Some microorganism see further increases in activity when salinity levels reach about 3% or less. Some reach their highest activity levels at even lower salinity levels, such as a level approaching what is considered fresh water (i.e., less than about 0.05% salt, by volume). Embodiments of the invention include increasing, as well as decreasing, the salinity level of water in the formation to reach a desired salinity level. For example, if the salinity level of the water is too low, salt amendments may be introduced (e.g., sodium chloride, potassium chloride, etc.) to increase the salinity.

Figure 6B:
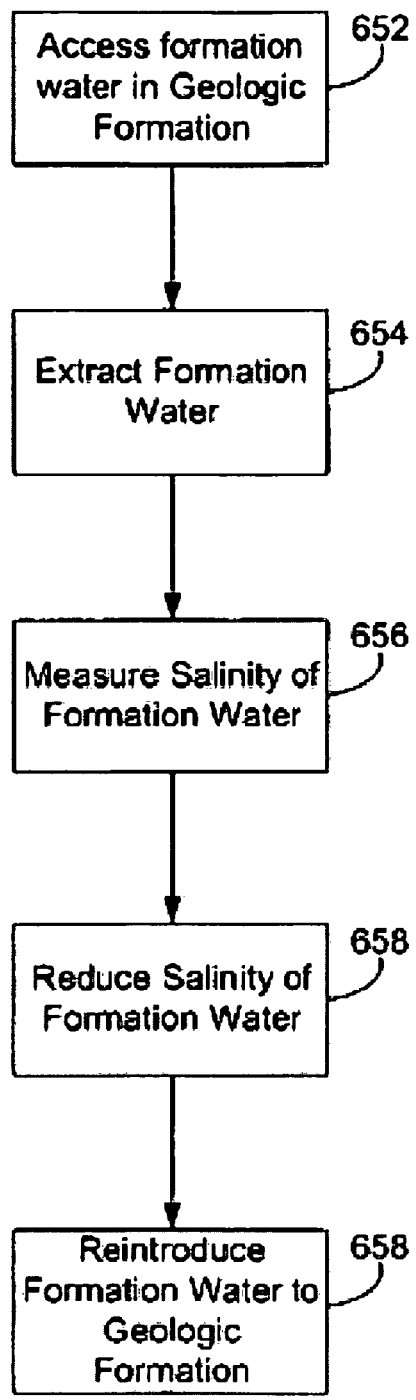

The water injected into the geological formation to change the salinity level of the water into the formation may come from an external source, or the formation itself. FIG. 6B is a flowchart illustrating steps in methods of changing the salinity by extracting, treating, and reintroducing water into same formation. The methods may include accessing the formation water in the geologic formation 652, and extracting a portion of the formation water 654. The salinity level of a sample of the extracted formation water is measured 656 to see if the water contains too much salt for significant metabolic production of carbon compound with enhanced hydrogen content.

If the salinity levels in the native formation water are too high, the extracted water may be treated to reduce the salinity level 658. A reduction in the salinity level of the water may be carried out by a variety of desalinization methods, including evaporation-condensation processes, multi-stage flash processes, electrodialysis reversal processes, reverse osmosis processes, freezing processes, and nanofiltration processes, among other processes. The desalinization process may reduce the salt concentration in the formation water to the level of fresh water (e.g, 0.05% or less salt, by volume), or end at higher salinity levels (e.g., about 2% salt, by vol., or less).

The reduced salinity formation water may then be reintroduced back into the geologic formation 658. Changes in the in situ salinity levels in the formation may be monitored during and after the reintroduction of the treated water. Concentrations and/or production rates for metabolite species in the formation (e.g., hydrogen, methane) may also be measured.

Embodiments of the invention also include extracting, desalinating, and reintroducing formation water to a geologic formation in an uninterrupted cycle. Thus, a first portion of native formation water may be extracted from the formation as a second portion is undergoing a desalinization process, and a third portion of treated water is being reintroduced to the formation, all at the same time. As additional cycles are completed, the salinity level of the formation water should be further reduced.

Definition of Salinity

Salinity is a measure of the dissolved salt concentration in water. The salts may include the dissolved ions of any ionic compounds present in the water. Common salts may include halide salts such as alkali metal halides (e.g., sodium chloride, potassium chloride, etc.) and alkali earth metal halides (e.g., magnesium chloride, calcium chloride, etc.). Salts may also include the salts of polyatomic cations and anions, such as ammonium salts, phosphate salts, nitrate salts, sulfate salts, and oxyhalide salts, among other kinds of salts.

The salinity level of "fresh water" is defined to have less than 0.05%, by vol, of salt. "Brackish water" has about 3% to 5% salt, by volume. "Brine" is defined as a concentrated salt solution that may be fully saturated at room temperature with one of more dissolved salt compound.

EXPERIMENTAL

Data presented herein demonstrate that anaerobic formation water obtained from any of several underground carbonaceous formations carries numerous MO's including a variety of MO species. Further, the data demonstrate that included among the MO's that can be collected from such water are all the species that make up a consortium capable of using a carbonaceous substrate, including coal, as a substrate to produce methane, under anaerobic conditions. Even though the number of MO's per liter of formation water may be low, large amounts of MO's can be accumulated by processing large volumes of water to collect the MO's therefrom.

Micro-organisms concentrated according to the invention are useful for biogenic production of methane from a carbonaceous substrate. Concentrated MO's can be used to generate methane under controlled conditions in an above-ground bioreactor, or used to enhance in situ methanogenesis. In either case, the methane that is generated can be used as a feedstock for chemical synthesis or used directly as a clean-burning fuel. The biogenic production of methane by the present invention requires minimal input of external energy.

Embodiments of the invention are further described in the following Experimental Examples.

Figure 8B:
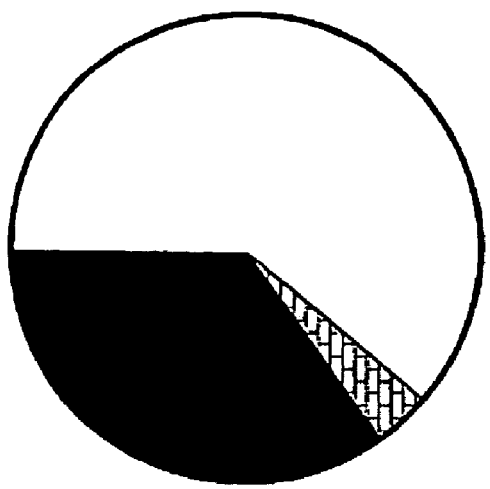
FIG. 8 shows two pie graphs showing the relative abundance of different microbial phospholipid types by conventional phospholipid fatty acid analysis (PLFA), comparing cells isolated from waters produced from The Tongue River Member of the Fort Union Formation located in the western edge of the Power River Basin of NE Wyoming, (left hand graph) with cells present in coals of the same formation (right hand graph). Total microbial biomass was $1.2 \times 10^5$ cells/ml Tongue River water, and $3 \times 10^6$ cells/g Tongue River coal, respectively.
Figure 8A:
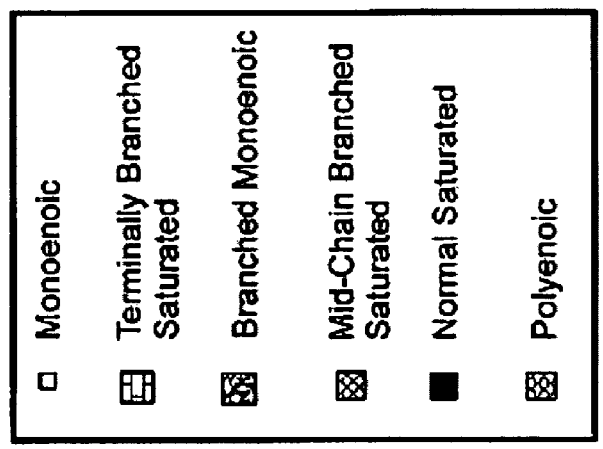
Figure 8A:
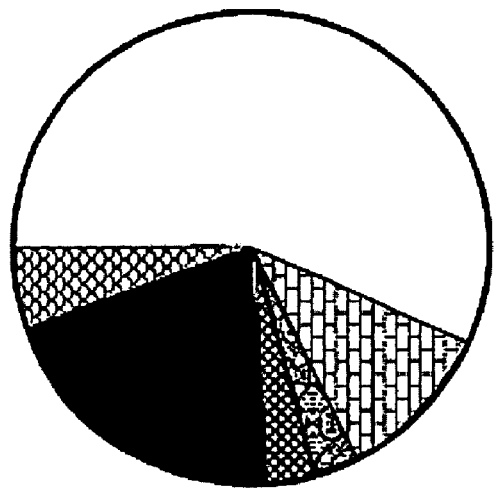

Quantification and Characterization of Microbial Biomass in Formation Waters of the Powder River Basin (PRB) Coal Bed Methane Development Area Four coal bed methane (CBM) water samples and six coal samples collected from the Tongue River area of the Powder River Basin in Wyoming were analyzed for phospholipid fatty acid analysis (PLFA). PLFA has proven to be an accurate tool for quantifying viable microbial biomass. The formation water samples were placed into sterile 4 L bottles with no headspace and spiked with a sterile sodium sulfide solution (to 0.5 mM) to preserve anoxic conditions. Oxygen exposure of the coal samples was minimized by storing them in gas tight cylinders that were purged with argon. FIG. 8 illustrates the microbial biomass estimates and community structure in both formation water and coal samples based on PLFA abundance and makeup respectively.

Microbial biomass in the formation water samples ranged from $7.65 \times 10^4$ cells/ml to $1.69 \times 10^5$ cells/ml with an average of $1 \times 10^5$ cells/ml. For comparison, microbial biomass in the coal samples ranged from $1.4 \times 10^6$ cells/g coal to $9.5 \times 10^6$ cells/g coal with an average of $3 \times 10^6$ cells/g coal. The microbial communities in formation water and in coal samples had similar PLFA compositions. These data indicate that the primary groups of microorganisms in the tested coals are also present in the associated formation waters.

Evaluation of Methods for Concentrating Microorganisms from Formation Waters of the PRB Microorganisms were concentrated from formation water obtained from a coal seam within the Powder River Basin (Tongue River area) using a hollow fiber tangential flow filtration column, and for comparison, by centrifugation.

The centrifugation procedure included several cycles of centrifuging formation water at 5500×G for 10 minutes in 60 ml centrifuge tubes. All sample manipulations were conducted in an anaerobic glove bag. A total volume of 1330 ml of formation water was centrifuged to 18.4 ml. The sample was analyzed by microscopy to ensure that microorganisms represented most of the turbidity (vs. coal fines or other particles).

The tangential flow procedure consisted of re-circulating 4 L Tongue River water through a tangential flow filtration column (0.2 vm pore size; 520 cm$^2$ surface area, by Spectrum Labs, part # M22E-101-015). Viton tubing, which has a very low oxygen permeability, and air tight (Swagelock) fittings were used for the flow lines and fittings respectively. A glass carboy purged with argon was used as the formation water holding vessel.

Three tests were performed to concentrate MO's from formation water at varying tangential total flow rates ranging from 370 mllmin to 2,300 mllmin (see Table 1). The permeate (filtered water leaving the tangential filter) flow rate ranged from 200 ml/minute to 614 ml/min. The efficiency of tangential flow for concentrating microorganisms from the formation water relative to centrifugation ranged from 95% to 155% (see the final column of Table 1). The final microbial biomass in the cell concentrates is in agreement with the cell concentration in the formation water. Thus, both centrifugation and tangential flow filtration were effective at concentrating microbial biomass from the formation water. Of particular interest is the final tangential flow test during which over 2 liters of water was filtered within approximately 3 minutes using a very small tangential flow filtration column. Concentrated MO's were active in formation water under refrigeration at 37° F. for at least 1 week.

TABLE 1

Comparison of centrifugation and tangential flow filtration for concentrating microbial biomass from formation water collected from a coal bed methane well.

| Total Flow Rate ml/min | Permeate Flow Rate (ml/min) | Volumetric Concentration | Cells/ml in Concentrate | Cell recovery efficiency relative to centerfugation |
|---|---|---|---|---|
| centrifuged | centrifuged | 80x | $5.8 \times 10^6$ | NA |
| 370 | 200 ml/min | 133x | $9.2 \times 10^6$ | 95% |
| 400 | 168 ml/min | 82x | $6.2 \times 10^6$ | 108% |
| 2,300 | 614 ml/min | 82x | $9.0 \times 10^6$ | 155% |

Methanogenesis Stimulated by Microorganisms Concentrated from CBM Waters

Figure 9:
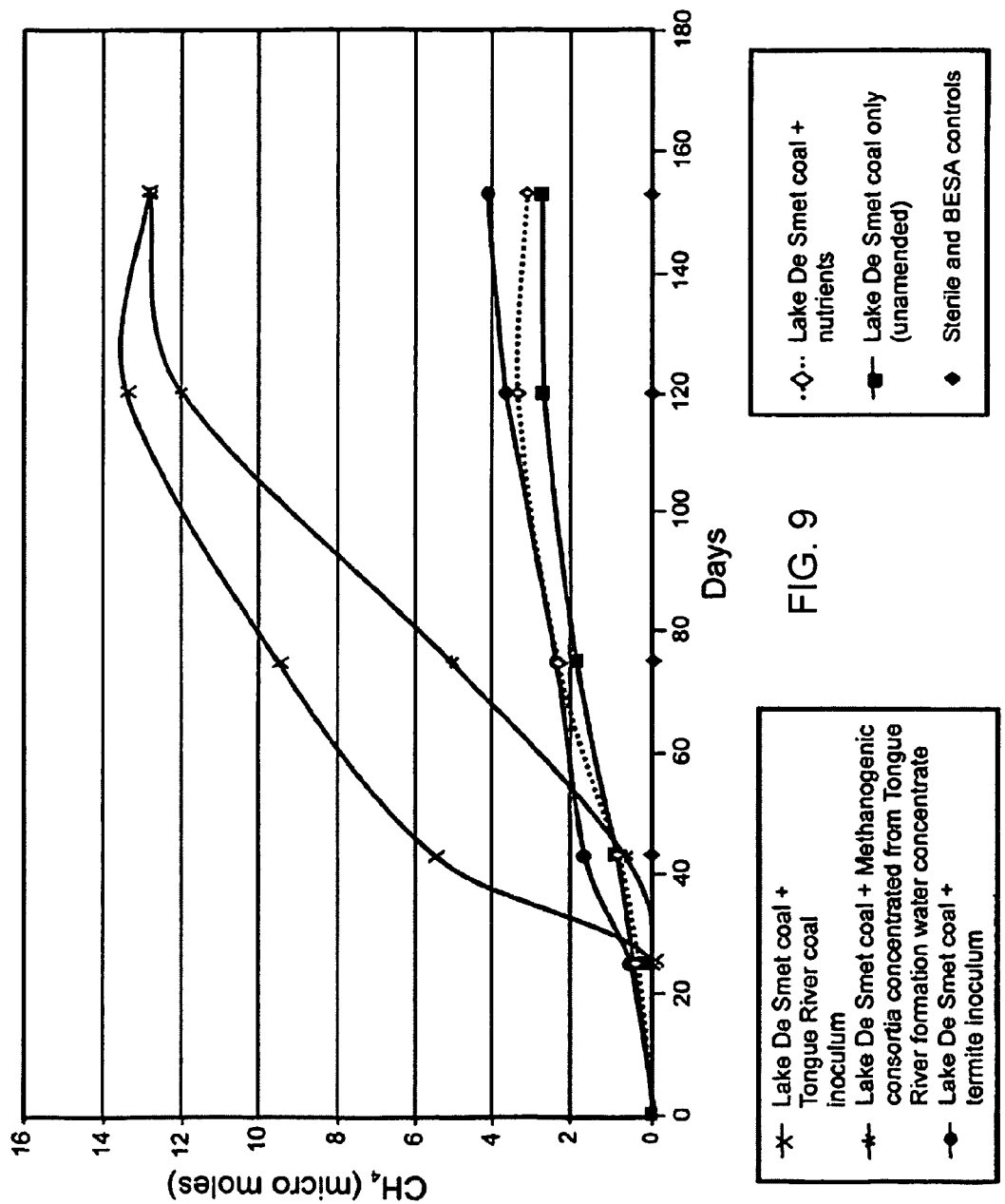
FIG. 9 is a graph of methane production as a function of time, from Lake De Smet coal, as described in the first Example, under various conditions as shown.

Experiments were conducted to test whether the introduction of microorganisms concentrated from the Tongue River formation water could stimulate the production of methane in coal slurries prepared with coal collected from the Lake De Smet region of the PRB. The Tongue River and Lake De Smet regions lie within the Powder River Basin about 35 miles apart from one another. While the Tongue River area has numerous active wells producing biogenic coal bed methane, generated through metabolic activity of indigenous consortia of MO's, the Lake De Smet region has none. Wells were drilled in the Lake De Smet region but subsequently abandoned because they were unproductive of methane. FIG. 9 illustrates the results of these experiments. All incubations were carried out at room temperature, which is similar to in situ formation temperatures. Methane production was detected and quantified by gas chromatography. Methane production was detected at relatively low rates in the coal slurries lacking added amendments (unamended controls) also in slurries having an added nutrient solution containing inorganic sources of nitrogen, phosphate, magnesium, calcium, potassium, a variety of metals, and a vitamin mixture. Methane production was not detected in sterilized slurries or in slurries amended with 2-bromoethane sulfonic acid to inhibit methanogenesis. After a short lag period methane production was stimulated significantly with the addition of microorganisms concentrated from the Tongue River formation water. The microbial biomass added to these slurries was equivalent to the number of microorganisms contained within 8.8 ml of Tongue River formation water. Methanogenesis was also stimulated after a lag period with the addition of Tongue River coal (0.5 g) added as a source of inoculum to the Lake De Smet coal slurries. The addition of a termite (*R. flavjpes*) hindgut cell suspension as a source of methanogenic consortium to the Lake De Smet coal slurries did not enhance methanogenesis significantly above the unamended coal slurries.

The quantity of cells that could be obtained by concentrating microorganisms from waters in the Powder River Basin (PRB) can be estimated by multiplying the concentration of microorganisms in the Tongue River formation water samples by total PRB CBM water production rate. Based on 44 million barrelslmonth ($6.9 \times 10^9$ L/month) produced in the PRB in 2004 and $1.2 \times 10^8$ cells/L average cell concentration in the Tongue River wells sampled, an estimated $8.4 \times 10^{17}$ cells can be recovered from all produced PRB CBM waters each month. The availability of such quantities of demonstrably active methanogenic consortium MO's, using the present invention, has established that it is practical and feasible to enhance methane production from carbonaceous formations, either by seeding a previously unproductive formation, or by stimulating a currently active formation.

Methanogenesis Stimulated by Changes in Water Dilution Levels

Laboratory experiments were done to measure how changes in the levels of formation water can effect methane production from coal extracted under anaerobic conditions from a subterranean coal seam. Formation water was also recovered from the formation under anaerobic conditions (i.e., the formation water samples were not exposed to ambient air).

Figure 7:
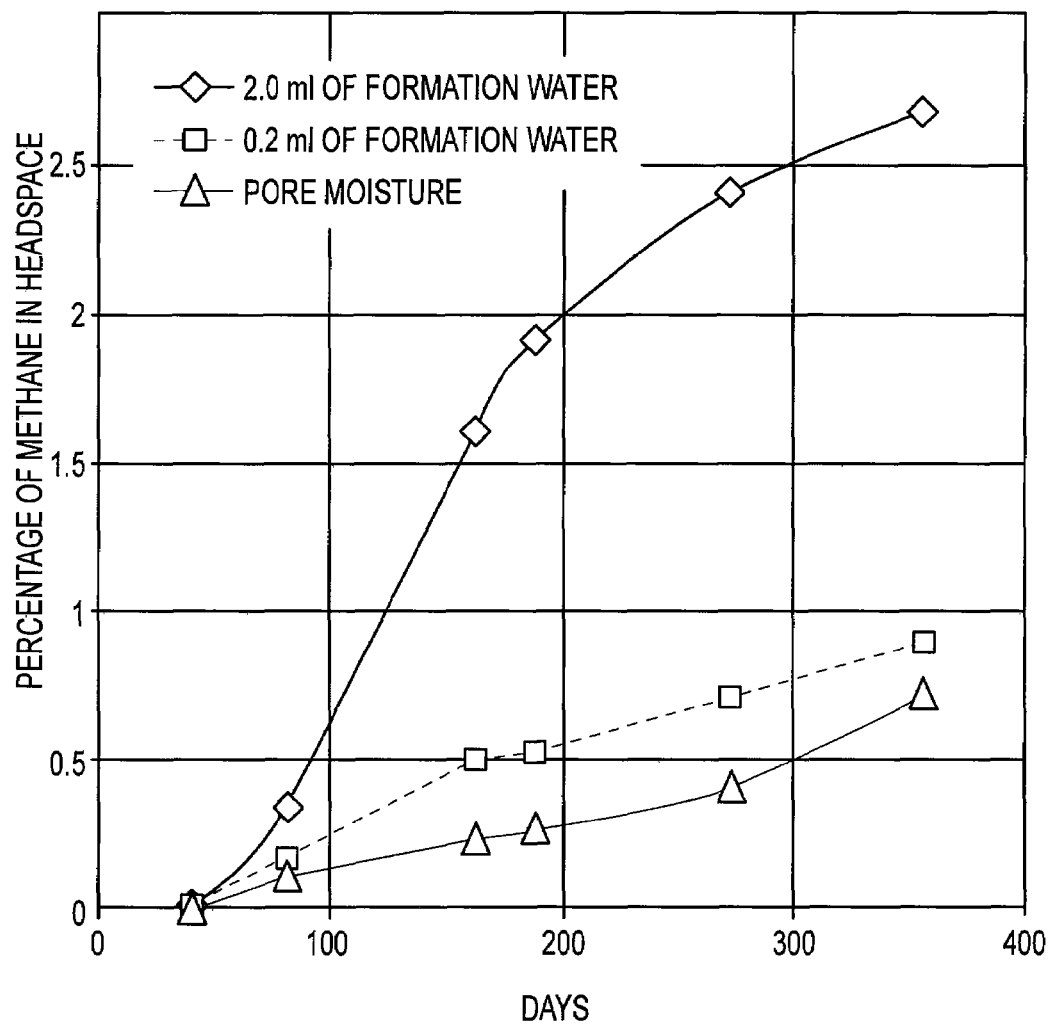
FIG. 7 is a plot of the percentage of methane in the headspace of a sealed coal container over time for three levels of added formation water.

Three coal samples of coal were taken from the Dietz Coal seam (North West quadrant of the Powder River Basin). All three samples were separately placed in 125 ml serum bottles that were sealed in an anaerobic environment of argon gas. No formation water was added to the first sample bottle, while 0.2 ml of formation water was injected into the second sample bottle, and 2.0 ml of formation water is injected into the third sample bottle. The percentage of methane measured in the headspace above the coal in the bottles was then measured over a 1 year period. FIG. 7 shows the plot of the percentage of methane in the headspace of the bottles over time for the three samples.

FIG. 7 clearly demonstrates that the addition of formation water stimulates the production of methane from the coal samples. Additional radiocarbon labeling studies provided strong evidence that the methane was being biogenically produced. Thus, this experiment shows that formation water can stimulate the biogenic production of methane from carbonaceous substrates like coal.

The Experiment shows that the addition of the formation water increased the percentage of methane nearly three-fold in about 150 days. The present invention contemplates systems and methods for amending and transporting formation water to carbonaceous materials in formations on commercial scales. A proportional scaling of the resulting increase in methane production will make these formations, which include dormant oil and coal fields, commercially viable sources of methane, hydrogen, and other metabolites from the microbial digestion of carbonaceous substrates.

Additional experiments are proposed to measure the effects of consortium dilution and metabolite amendments on the production of biogenic gases. These include a first set of experiments for injecting water into a geologic formation containing coal. The coal deposit is an "active" coal that has been shown to produce methane from either biogenic processes (e.g., methanogenic microorganisms) or non-biogenic processes (e.g., methane desorption off the substrate, thermal breakdown of substrate, etc.). The water may be fresh water or salt water that has been filtered of microorganisms. This set of experiments compares changes in the rate of methane and hydrogen off-gassing based on how the water is introduced to the coal. For example, in one experiment, larger volumes of water are injected at higher pressure in fewer cycles, while a second experiment injects smaller volumes at lower pressure in more cycles. In these "huff and puff" experiments, fluids building up in the formation may also be extracted from between injection events. The measurements of the changes in the rates at which methane, hydrogen and other gases are building up in the formation offer insight into how a consortium of native microorganisms responds to the different patterns for water injection and extraction cycles.

A second set of experiments compares changes in the rate of methane and hydrogen off-gassing after introducing water to both active and inactive coals. The active coals demonstrated significant methane off-gassing prior to introducing the water, while the inactive coals showed very little pre-water off-gassing. The water used in these experiments is extracted from the formation itself and the native microorganism are not filtered or killed. In some experiments, the formation water may be extracted from the part of the formation in contact with the coal, while in others the water is taken from a different part of the formation. Different patterns of water injection cycles may also be compared for both the active and coal coals in this set of experiments.

A third set of experiments measures the effect of specific nutrient amendments on the rate of off-gassing from a deposit of active coal in a geologic formation. The nutrient amendments are added to water that's injected into the formation and onto the coal. The amendments may include a high concentration of yeast extract, a low concentration of yeast extract and phosphorous in various combinations. The water used comes for the formation. The same injection pattern is used for introducing the amended water to the coal to better attribute and correlate differences in off-gassing rates to the type of amendment used.

A fourth set of experiments introduces microorganism concentrates to an inactive coal deposit and measures changes in the off-gassing of gases such as hydrogen and methane. The microorganism concentrate may come from the retentate of filtered formation water. The experiments may use different injection patterns to introduce the microorganisms to the coal. The experiments may also dilute the concentrate to various levels (e.g., diluting the concentrate to 50%, 25%, 10%, etc., of its original concentration) to measure the effects of this dilution on the concentrate's ability to stimulate biogenic gas production.

A fifth set of experiments introduces hydrogen gas to the coals and measures its effect on the rate of off-gassing of methane. The experiments include introducing the hydrogen gas to both active and inactive coals. The hydrogen gas may be introduced after water has been introduced to the coals. In some of the experiments, microorganisms may also be introduced to the coal before its exposed to the hydrogen gas, or simultaneously therewith. Nutrient amendments, such as vitamins, minerals, yeast extract, phosphorous, phosphate, etc., may also be added.

A sixth set of experiments introduces acetate to the coals and measures its effect on the rate of off-gassing from the coal. The acetate may be introduced as an aqueous solution of acetic acid that's injected into the formation and onto the coal. Similar to the hydrogen gas experiments, the acetate experiments may be conducted on both active and inactive coals. Some of the experiments may include introducing microorganisms to the coal as well.

Tables 2A and B lists some of the experimental parameters for the six sets of experiments described above. It should be appreciated that the list in Tables 1A and B are not exhaustive, and different combinations of parameters (as well and additional parameters) may also be tried.

TABLE 2A

Experimental Parameters for Six Sets of Experiments

| Experimental Set | Treatment Summary | Cells In Treatment | Cells Grown on Surface | Nutrient Addition | Water Source | Cells Filtered Out | Cell Concentrate Added |
|---|---|---|---|---|---|---|---|
| First | Fresh Water | Formation | No | None | Any Water | Yes | No |
| First | Fresh Water | Formation | No | None | Any Water | Yes | No |
| Second | Water Flush | Formation | No | None | Same Well | None | No |
| Second | Water Flush | Formation | No | None | Same Well | None | No |
| Second | Water Flush | Formation | No | None | Same Formation | None | No |
| Second | Water Flush | Formation | No | None | Same Formation | None | No |
| Third | Nutritional | Formation & Water | No | High YE | Same Formation | None | No |
| Third | Nutritional | Formation & Water | No | Low YE | Same Formation | None | No |
| Third | Nutritional | Formation & Water | No | P | Same Formation | None | No |
| Third | Nutritional | Formation & Water | No | High YE + P | Same Formation | None | No |
| Third | Nutritional | Formation & Water | No | Low YE + P | Same Formation | None | No |
| Fourth | Inoculation | Cell Conc. | No | Low MMV | Specific to cells | Yes | Yes |
| Fourth | Inoculation | Cell Conc. | No | Low MMV | Specific to Cells | Yes | Yes |
| Fourth | Grow and Dliute | Cell Conc. | No | Low MMV | Any Water | Yes | Yes - Diluted |

TABLE 2A-continued

Experimental Parameters for Six Sets of Experiments

| Experimental Set | Treatment Summary | Cells In Treatment | Cells Grown on Surface | Nutrient Addition | Water Source | Cells Filtered Out | Cell Concentrate Added |
|---|---|---|---|---|---|---|---|
| Fifth | H$_2$ Add Formation | Formation | No | Low MMV | Same Well | Yes | No |
| Fifth | H$_2$ Add Both | Formation & Water | No | Low MMV | Same Well | No | No |
| Fifth | H$_2$ Add Water | Water | Yes | Low MMV | Same Formation | No | No |
| Fifth | H$_2$ Add New Cells | Water | Yes | Low MMV | Any Water | Yes | Yes |
| Sixth | Acetate Add | Formation | No | Low MMV | Same Well | Yes | No |
| Sixth | Acetate Add | Formation & Water | No | Low MMV | Same Well | No | No |
| Sixth | Acetate Add | Water | Yes | Low MMV | Same Formation | No | No |
| Sixth | Acetate Add | Water | Yes | Low MMV | Any Water | Yes | Yes |

TABLE 2-B

Experimental Parameters for Six Sets of Experiments (con't)

| Experimental Set | Number of Injection Cycles | Big or Small Injection Volume | High or Low Pressure | Water Level Over Coal | Active Coal | Water Wash First? | Number of Wells |
|---|---|---|---|---|---|---|---|
| First | Several | Small | Low | No | Yes | N/A | Few |
| First | Few | Big | High | No | Yes | N/A | Several |
| Second | Several | Small | Low | No | Yes | No | Several |
| Second | Few | Big | High | No | No | No | Several |
| Second | Several | Small | Low | No | Yes | No | Few |
| Second | Few | Big | High | No | No | No | Several |
| Third | Few | Big | High | No | Yes | No | Several |
| Third | Few | Big | High | No | Yes | No | Several |
| Third | Few | Big | High | No | Yes | No | Several |
| Third | Few | Big | High | No | Yes | No | Several |
| Third | Few | Big | High | No | Yes | No | Several |
| Fourth | Several | Small | Low | No | No | Maybe | Few |
| Fourth | Few | Big | High | No | No | Maybe | Several |
| Fourth | Several | Small | Low | No | No | Yes | Few |
| Fifth | Several | Small | Low | Yes | Yes | Maybe | Few |
| Fifth | Several | Small | Low | Yes | No | Maybe | Few |
| Fifth | Several | Small | Low | No | No | Yes | Few |
| Fifth | Several | Small | Low | No | No | Yes | Few |
| Sixth | Several | Small | Low | No | Yes | Maybe | Few |
| Sixth | Several | Small | Low | No | No | Maybe | Few |
| Sixth | Several | Small | Low | No | No | Yes | Few |
| Sixth | Several | Small | Low | No | No | Yes | Few |

In Tables 2A-B the nutrient addition "MMV" indicates metals, minerals and/or vitamin amendment was made; "YE" indicates a yeast extract amendment was made; and "P" indicates phosphate amendment was made.

Examples of mineral amendments may include the addition of chloride, ammonium, phosphate, sodium, magnesium, potassium, and/or calcium to the isolate, among other kinds of minerals. Metal amendments may include the addition of manganese, iron, cobalt, zinc, copper, nickel, selenate, tungstenate, and/or molybdate to the isolate, among other kinds of metals. Vitamin amendments may include the addition of pyridoxine, thiamine, riboflavin, calcium pantothenate, thioctic acid, p-aminobenzoic acid, nicotinic acid, vitamin B12, 2-mercaptoehanesulfonic acid, biotin, and/or folic acid, among other vitamins. The addition of these amendments may involve adding mineral salts, metal salts, and vitamins directly to the isolate, or first preparing a solution of the salts and vitamins that then gets added to the isolate.

The concentration of the MMV, YE and P amendments may depend on the concentration and composition of an isolated consortium. Examples of concentration ranges for amendment components may include about 1 mg/L to about 500 mg/L for mineral amendment; about 10 µg/L to about 2000 µg/L for a metal amendment; and about 1 µg/L to about 100 µg/L for a vitamin amendment.

Having described several embodiments, it will be recognized by those of skill in the art that various modifications, alternative constructions, and equivalents may be used without departing from the spirit of the invention. Additionally, a number of well known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the electrode" includes reference to one or more electrodes and equivalents thereof known to those skilled in the art, and so forth.

The term "micro-organism" is used in its broadest and generally understood sense to mean any living organism that is too small to be seen with the naked eye. MO's are found in almost all samples of underground material, either dispersed in subterranean water or adsorbed on or adhering to solid material. Of particular interest in the present invention are MO1s suspended in underground water, especially water obtained from carbonaceous formations, more particularly, water obtained from an anaerobic region of a methane-producing carbonaceous formation. Such water is termed "anaerobic formation water" herein.

A "carbonaceous formation" may include any place on or under the earth's surface whose composition is rich in hydrocarbons, including but not limited to coal, bitumen, oil shale, carbonaceous shale, tar sands, peat, oil and/or gas deposits, sediments rich in organic matter and the like. "Formation water" is water found within, or obtained from a carbonaceous formation. "Anaerobic" formation water is characterized as having little or no dissolved oxygen, in general no more than 4 mg/L, preferably less than 2 mg/L, most preferably less than 0.1 mg/L, as measured at 20 degrees C. and 760 mmHg barometric pressure. During application of the present invention, higher levels of dissolved oxygen, greater than 4 mg/L, can be tolerated without appreciably degrading consortium performance, for limited times or in certain locations such as a surface layer in a storage or settling tank. Dissolved oxygen can be measured by well-known methods, such as by commercially-available electrodes, or by the well-known Winkler reaction. It will be understood that carbonaceous formations can have both aerobic regions and anaerobic regions. For example, a coal deposit is likely to be aerobic near a surface exposed to air by mining activity. At a depth below the exposed surface, the deposit, including associated formation waters becomes anaerobic. Such water is what is termed herein "anaerobic formation water."

"Contacting" refers to any process which results in bringing a methanogenic consortium into surface contact with carbonaceous material.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method for stimulating methane production from a carbonaceous material comprising the steps of
   a) contacting the material with cells of a methanogenic consortium under anaerobic conditions, forming a reaction mixture,
   b) maintaining anaerobic conditions for a time sufficient to permit methanogenesis, and
   c) collecting methane from anaerobic water or head space of the reaction mixture,
   wherein the consortium is a concentrate of microorganisms prepared by the method of:
   i) extracting anaerobic formation water containing said microorganisms from an underground carbonaceous formation,
   ii) providing liquid transport means for transporting said water while maintaining an anaerobic state,
   iii) providing collection means for collecting said microorganisms in an anaerobic state from said water,
   iv) transporting said water through said collection means whereby said microorganisms are collected from said water, and
   v) removing said microorganisms in a concentrated form in said water from the collection means, whereby a concentrate of said microorganisms is prepared.

2. The method of claim 1 wherein the carbonaceous material is present in situ in an underground formation.

3. The method of claim 1 wherein the carbonaceous material is extracted from an underground formation.

4. The method of claim 1 wherein the methanogenic consortium is essentially sediment-free.

5. The method of claim 1 wherein the concentrate has at least ten times more microorganisms per unit volume formation water than the formation water of step (a).

6. The method of claim 1 wherein the anaerobic formation water is obtained from a methane-producing formation.

7. A method of preparing a concentrate of microorganisms comprising a consortium of methanogenic microorganisms, comprising the steps of,
   a) extracting anaerobic formation water containing said microorganisms from an underground carbonaceous formation,
   b) providing liquid transport means for transporting said water while maintaining an anaerobic state,
   c) providing collection means for collecting said microorganisms in an anaerobic state from said water,
   d) transporting said water through said collection means, whereby said micro-organisms are collected from said water, and
   e) removing said microorganisms in a concentrated form in said water from the collection means, whereby a concentrate of said microorganisms is prepared.

8. The method of claim 7 wherein the collection means comprises tangential filtration.

9. The method of claim 7 wherein the collection means comprises centrifugation.

10. The method of claim 7 wherein the concentrate has at least ten times more microorganisms per unit volume than formation water of step (a).

11. The method of claim 7 wherein the concentration contains at least 108 cells/ml.

* * * * *

UNITED STATES PATENT AND TRADEMARK OFFICE
CERTIFICATE OF CORRECTION

PATENT NO. : 7,640,978 B2 Page 1 of 1
APPLICATION NO. : 12/136728
DATED : January 5, 2010
INVENTOR(S) : Pfeiffer et al.

It is certified that error appears in the above-identified patent and that said Letters Patent is hereby corrected as shown below:

Title page, Item [56] References Cited, U.S. Patent Documents, add --2,185,216 5/1965 Hitzman--

Signed and Sealed this

Sixteenth Day of March, 2010

David J. Kappos
*Director of the United States Patent and Trademark Office*